(12) United States Patent
Huijbregts et al.

(10) Patent No.: US 11,678,809 B2
(45) Date of Patent: Jun. 20, 2023

(54) APPARATUS AND METHOD FOR DETERMINING A CALIBRATION PARAMETER FOR A BLOOD PRESSURE MEASUREMENT DEVICE

(71) Applicant: KONINKLIJKE PHILIPS N.V., Eindhoven (NL)

(72) Inventors: Laurentia Johanna Huijbregts, Eindhoven (NL); Jens Muehlsteff, Aachen (DE); Lars Schmitt, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1042 days.

(21) Appl. No.: 16/466,424

(22) PCT Filed: Dec. 5, 2017

(86) PCT No.: PCT/EP2017/081576
§ 371 (c)(1),
(2) Date: Jun. 4, 2019

(87) PCT Pub. No.: WO2018/104337
PCT Pub. Date: Jun. 14, 2018

(65) Prior Publication Data
US 2019/0343407 A1    Nov. 14, 2019

(30) Foreign Application Priority Data
Dec. 9, 2016   (EP) ..................................... 16203137

(51) Int. Cl.
*A61B 5/021*   (2006.01)
*A61B 5/11*    (2006.01)
*A61B 5/00*    (2006.01)

(52) U.S. Cl.
CPC ........ *A61B 5/02125* (2013.01); *A61B 5/1116* (2013.01); *A61B 5/70* (2013.01); *A61B 5/7278* (2013.01); *A61B 2560/0223* (2013.01)

(58) Field of Classification Search
CPC .... A61B 2560/0223; A61B 2560/0238; A61B 5/02108; A61B 5/02125; A61B 5/1116; A61B 5/70; A61B 5/7278
See application file for complete search history.

(56) References Cited

U.S. PATENT DOCUMENTS 8,672,854 B2   3/2014   McCombie et al.
8,838,209 B2   9/2014   Mestha et al.
(Continued)

FOREIGN PATENT DOCUMENTS

CN   101088455 A  *  6/2006   ............. A61B 5/021
CN   101088455 A     12/2007
(Continued)

OTHER PUBLICATIONS

Muehlsteff, J. et al., "Continuous Cuff-less Blood Pressure Monitoring based on the Pulse Arrival Time Approach: The Impact of Posture", Engineering in Medicine and Biology Society, 2008, 30th Annual IEEE.

(Continued)

*Primary Examiner* — Yi-Shan Yang
*Assistant Examiner* — Alexei Bykhovski

(57) ABSTRACT

According to an aspect there is provided a method of determining a calibration parameter for a first blood pressure, BP, measurement device, the method comprising obtaining a first physiological characteristic measurement of a subject using the first BP measurement device, wherein the first BP measurement device is for obtaining physiological characteristic measurements of a physiological characteristic of the subject and for determining a BP measurement of (Continued)

the subject from the physiological characteristic measurements using the calibration parameter, wherein the first physiological characteristic measurement is obtained when a torso of the subject is in a first posture; obtaining a second physiological characteristic measurement of the subject using the first BP measurement device, wherein the second physiological characteristic measurement is obtained when the torso of the subject is in a second, different, posture; determining the change in the posture of the torso from the first posture to the second posture; estimating a change in BP of the subject or a change in the physiological characteristic of the subject from the determined change in the posture of the torso; and determining the calibration parameter for determining BP measurements from physiological characteristic measurements obtained by the first BP measurement device from an analysis of the first physiological characteristic measurement, the second physiological characteristic measurement and the estimated change.

15 Claims, 9 Drawing Sheets

(56) References Cited

U.S. PATENT DOCUMENTS

| | | |
|---|---|---|
| 2002/0188205 A1 | 12/2002 | Mills |
| 2011/0144456 A1 | 6/2011 | Muhlsteff et al. |
| 2013/0338519 A1* | 12/2013 | Chen .................... A61B 5/366 600/509 |
| 2014/0276175 A1 | 9/2014 | Banet et al. |
| 2015/0327784 A1 | 11/2015 | Lading et al. |
| 2016/0015329 A1* | 1/2016 | Kohlrausch ............ A61B 5/002 340/573.4 |
| 2016/0143545 A1 | 5/2016 | Nishihara et al. |
| 2016/0143546 A1* | 5/2016 | McCombie ........ A61B 5/02125 600/494 |
| 2016/0220122 A1 | 8/2016 | Luna et al. |

FOREIGN PATENT DOCUMENTS

| | | |
|---|---|---|
| DE | 102010014761 A1 | 10/2011 |
| EP | 2921104 A1 | 9/2015 |
| WO | 2012092303 A1 | 7/2012 |

OTHER PUBLICATIONS

International Search Report and Written Opinion, International Application No. PCT/EP2017/081576, dated Feb. 19, 2018.

Butlin, M., et al., "A simplified method for quantifying the subject-specific relationship between blood pressure and carotid-femoral pulse wave velocity", Annual International Conference of the IEEE Engineering in Medicine and Biology Society, Aug. 2015.

Patel, S. et al., "A review of wearable sensors and systems with application in rehabilitation", Journal of NeuroEngineering and Rehabilitation, 2012, 9:21.

Viera, A. et al., "Tolerability of the Oscar 2 ambulatory blood pressure monitor among research participants: a cross-sectional repeated measures study", BMC Medical Research Methodology, 2011, 11:59.

Muehlsteff, J. et al., "Comparison of pulse wave velocity derived from accelerometer and reflective photo-plethysmography signals placed at the carotid and femoral artery", EMBC, 2016.

"Central Blood Pressure", https://www.uscom.com.au/products/bp/education, Accessed Jun. 2019.

M.J. Roman, et al., "Central Pressure More Strongly Relates to Vascular Disease and Outcome Than Does Brachial Pressure. The Strong Heart Study," Hypertension, May 2007.

M.J. Roman et al., "High Central Pulse Pressure is Independently Associated With Adverse Cardiovascular Outcome The Strong Heart Study," J Am Coll Cardiol, vol. 54, Oct. 2009, pp. 1730-1734.

A. Avolio, "Central Aortic Blood Pressure and Cardiovascular Risk: A Paradigm Shift?," Hypertension, vol. 51, Jun. 2008, pp. 1470-1471.

P. Boutouyrie, et al., "Amlodipine-Valsartan Combination Decreases Central Systolic Blood Pressure More Effectively Than the Amlodipine-Atenolol Combination: The Explor Study," Hypertension, vol. 55, Jun. 2010, pp. 1314-1322.

* cited by examiner (a)

(b)

APPARATUS AND METHOD FOR DETERMINING A CALIBRATION PARAMETER FOR A BLOOD PRESSURE MEASUREMENT DEVICE

CROSS-REFERENCE TO PRIOR APPLICATIONS

This application is the U.S. National Phase application under 35 U.S.C. § 371 of International Application No. PCT/EP2017/081576, filed on 5 Dec. 2017, which claims the benefit of European Patent Application No. 16203137.1, filed on 9 Dec. 2016. These applications are hereby incorporated by reference herein.

TECHNICAL FIELD OF THE INVENTION

The invention relates to a blood pressure measurement device that is used to obtain measurements of the blood pressure of a subject, and in particular relates to an apparatus and method for determining a calibration parameter for the blood pressure measurement device.

BACKGROUND TO THE INVENTION

A commonly-measured vital sign that can provide an indication of a person's condition is blood pressure (BP). BP can provide information on the hemodynamic status of the person and can be used to detect critical situations, deterioration or cardio-vascular diseases. BP is usually measured with an arm cuff (for example automatically by using the oscillometric technique, which involves analysis of the amplitude of the pressure changes in the cuff due to the blood pulse, or manually by using the auscultatory technique, which involves the detection of Korotkoff sounds).

However, measuring BP with an arm cuff has several disadvantages. For example, it cannot be used to measure BP continuously, but is instead used for spot checks or for obtaining measurements at regular intervals (but always having at least several minutes in between each measurement). Therefore, sudden hemodynamic changes, which especially can occur in the intensive care unit (ICU) or operating room (OR) and which need immediate intervention, may often only be noticed after several minutes. For this reason, it is desired to provide other methods that can measure BP continuously. Another disadvantage is that when the cuff is worn for more than an hour while taking BP measurements, e.g. every 15 minutes, such as in ambulatory blood pressure monitoring (ABPM), the cuff can cause pain, skin irritation and bruising. Having to wear a cuff also puts constraints on the clothes that the subject can wear, e.g. since the cuff should be worn on a bare arm or over a thin sleeve. Inflation of the cuff during the night often wakes up the user. Finally, a cuff-based measurement measures blood pressure in the periphery of the body (i.e. in an arm or leg), rather than in a central part of the body (i.e. in the torso or chest).

An alternative to a cuff-based measurement is the use of an invasive line, which addresses many of the drawbacks with cuff-based measurements, but has its own disadvantages, namely infection risk, the need for experienced clinical staff to apply the invasive line, and reduced mobility for the subject.

Therefore it is desirable to use a blood pressure measurement technique that is non-invasive and continuous (i.e. that allows a blood pressure measurement to be obtained continuously).

Several techniques for obtaining continuous blood pressure measurements in a non-invasive manner exist. For example blood pressure measurements can be obtained from a measurement of pulse wave velocity (PWV), pulse transit times (PTT), pulse arrival times (PAT) or from features in a photoplethysmography (PPG) signal. In contrast to the invasive line or oscillometric/auscultatory-based methods above, which provide direct measurements of the blood pressure, these blood pressure measurements provide an indirect measurement of blood pressure, and are thus referred to herein as 'surrogate' blood pressure measurements. However, it is necessary for the mathematical relationship that relates blood pressure to a non-invasive continuous surrogate blood pressure measurement to be calibrated regularly in order to obtain accurate measurements of the blood pressure because these surrogate measurements can be influenced by physiological changes other than changes in the blood pressure.

SUMMARY OF THE INVENTION

To obtain a reliable calibration, measurements of the surrogate and blood pressure at two different blood pressure levels are required (as a minimum). In some cases it can be acceptable to perform the calibration over a significant period of time (e.g. a few hours or days), but in other cases it is desirable to perform the calibration much quicker (e.g. in the case of a blood pressure measurement device used in an ICU or OR). In this case a change in the blood pressure of the subject needs to occur to allow measurements of blood pressure to be made at two or more different levels.

U.S. Pat. No. 8,672,854 describes calibrating a PTT-based blood pressure measurement using changes in a patient's arm height, and in particular determining features from a time-dependent waveform that is indicative of contractile properties of the heart at two different arm positions. However, this technique has some disadvantages. For example, this method only works when the surrogate measurement is taken on the arm. This gives a so-called 'peripheral blood pressure' because the brachial artery is a peripheral artery. On the other hand, central blood pressure is the pressure in the aorta, which is the large artery into which the heart pumps. The term 'central blood pressure' usually refers to the pressure in the aorta near the heart. Peripheral blood pressure in terms of systolic and pulse pressure is usually higher than central blood pressure due to the peripheral site being closer to locations from which reflections reverberate. The degree to which the peripheral blood pressure is higher than central blood pressure depends partly on the stiffness of the arteries. A central blood pressure measurement is preferred because central pressure has been shown to more strongly relate to vascular disease and outcome than traditional measurements of blood pressure from the upper arm, and it also can distinguish between the effects of different hypertension medications, which upper arm blood pressure measurements do not.

There is therefore a need for an improved method and apparatus for calibrating measurements of blood pressure obtained by a blood pressure measurement device, for example a blood pressure measurement device that obtains a central measurement of blood pressure, and in particular for determining a calibration parameter for the blood pressure measurement device.

According to a first aspect, there is provided a method of determining a calibration parameter for a first blood pressure, BP, measurement device, the method comprising obtaining a first physiological characteristic measurement of a subject using the first BP measurement device, wherein the first BP measurement device is for obtaining physiological characteristic measurements of a physiological characteristic of the subject and for determining a BP measurement of the subject from the physiological characteristic measurements using the calibration parameter, wherein the first physiological characteristic measurement is obtained when a torso of the subject is in a first posture; obtaining a second physiological characteristic measurement of the subject using the first BP measurement device, wherein the second physiological characteristic measurement is obtained when the torso of the subject is in a second, different, posture; determining the change in the posture of the torso from the first posture to the second posture; estimating a change in BP of the subject or a change in the physiological characteristic of the subject from the determined change in the posture of the torso; and determining the calibration parameter for determining BP measurements from physiological characteristic measurements obtained by the first BP measurement device from an analysis of the first physiological characteristic measurement, the second physiological characteristic measurement and the estimated change.

In some embodiments, the method further comprises the step of monitoring the posture of the torso of the subject to identify a change in the posture of the torso from the first posture to a second posture; wherein the step of obtaining the second physiological characteristic measurement is performed in response to identifying the change in the posture of the torso to the second posture.

In some embodiments, the method further comprises, after the step of obtaining the first physiological characteristic measurement, the step of causing a change in the posture of the torso of the subject from the first posture to the second posture.

In some embodiments, the step of causing the change in the posture comprises providing an instruction or command to the subject or a care provider for the subject that the posture of the torso of the subject is to be changed. In alternative embodiments, the step of causing the change in the posture comprises outputting a control signal to an actuator for a bed or chair associated with the subject to change the angle of the bed or chair.

In some embodiments, the step of determining the change in the posture of the torso from the first posture to the second posture comprises analysing a measurement signal from a posture sensor.

In alternative embodiments, the first BP measurement device comprises a physiological characteristic sensor for measuring the physiological characteristic of the subject, and wherein the step of determining the change in the posture of the torso from the first posture to the second posture comprises analysing a measurement signal from the physiological characteristic sensor.

In some embodiments, the step estimating a change in BP of the subject from the determined change in the posture of the torso comprises estimating a change in height of a location on the body at which the physiological characteristic is measured relative to a heart of the subject from the first posture to the second posture based on the determined change in posture.

In alternative embodiments, the physiological characteristic is pulse transit time, PTT, that is obtained by measurements of pulse arrival at two different locations on the body of the subject that are separated by a length l, and wherein the step of estimating a change in the physiological characteristic of the subject from the determined change in the posture of the torso comprises evaluating $$PTT(\alpha) = -\frac{1}{m\rho g \sin(\alpha)} \ln\left|1 - \frac{m\rho g l \sin(\alpha)}{mP+n}\right|$$

for each of the first and second postures, where ρ is the density of blood, g is acceleration due to gravity, P is the blood pressure, α is the angle of the torso with respect to the horizontal and m and n are calibration parameters.

In some embodiments, the first BP measurement device is a BP measurement device that can be used to obtain a continuous or semi-continuous measurement of BP.

In some embodiments, the physiological characteristic measured by the first BP measurement device provides a surrogate measurement of BP.

In some embodiments, the physiological characteristic is one or more characteristics of a Photoplethysmogram, PPG, signal, a pulse wave velocity, a pulse arrival time, or a pulse transit time.

In some embodiments, the method further comprises the step of obtaining a BP measurement of the subject from a third physiological characteristic measurement by the first BP measurement device and the determined calibration parameter.

In some embodiments, after obtaining the first physiological characteristic measurement, the method comprises analysing a signal from the first BP measurement device to determine whether the physiological characteristic is stable; and obtaining the second physiological characteristic measurement if the physiological characteristic is determined to be stable.

According to a second aspect, there is provided a computer program product comprising a computer readable medium having computer readable code embodied therein, the computer readable code being configured such that, on execution by a suitable computer or processor, the computer or processor is caused to perform any of the methods described above.

According to a third aspect, there is provided an apparatus for determining a calibration parameter for a first blood pressure, BP, measurement device, the apparatus comprising a control unit that is to be coupled to a first BP measurement device that is for obtaining physiological characteristic measurements of a physiological characteristic of a subject and for determining a blood pressure measurement of the subject from the physiological characteristic measurements, wherein the control unit is configured to obtain a first physiological characteristic measurement of the subject using the first BP measurement device, wherein the first physiological characteristic measurement is obtained when a torso of the subject is in a first posture; obtain a second physiological characteristic measurement of the subject using the first BP measurement device, wherein the second physiological characteristic measurement is obtained when the torso of the subject is in a second, different, posture; determine the change in the posture of the torso from the first posture to the second posture; estimate a change in BP of the subject or a change in the physiological characteristic of the subject from the determined change in the posture of the torso; and determine the calibration parameter for determining BP measurements from physiological characteristic measurements obtained by the first BP measurement device from an analysis of the first physiological characteristic measurement, the second physiological characteristic measurement and the estimated change.

In some embodiments, the control unit is further configured to monitor the posture of the torso of the subject to identify a change in the posture of the torso from the first posture to a second posture; wherein the control unit is configured to obtain the second physiological characteristic measurement in response to identifying a change in the posture of the torso to the second posture.

In some embodiments, the control unit is further configured to cause a change in the posture of the torso of the subject from the first posture to the second posture after the first physiological characteristic measurement is obtained.

In some embodiments, the control unit is configured to cause the change in the posture by providing an instruction or command to the subject or a care provider for the subject that the posture of the torso of the subject is to be changed. In alternative embodiments, the control unit is configured to cause the change in the posture by outputting a control signal to an actuator for a bed or chair associated with the subject to change the angle of the bed or chair.

In some embodiments, the control unit is configured to determine the change in the posture of the torso from the first posture to the second posture by analysing a measurement signal from a posture sensor.

In alternative embodiments, the first BP measurement device comprises a physiological characteristic sensor for measuring the physiological characteristic of the subject, and wherein the control unit is configured to determine the change in the posture of the torso from the first posture to the second posture by analysing a measurement signal from the physiological characteristic sensor.

In some embodiments, the control unit is configured to estimate a change in BP of the subject from the determined change in the posture of the torso by estimating a change in height of a location on the body at which the physiological characteristic is measured relative to a heart of the subject from the first posture to the second posture based on the determined change in posture.

In alternative embodiments, the physiological characteristic is pulse transit time, PTT, that is obtained by measurements of pulse arrival at two different locations on the body of the subject that are separated by a length l, and wherein the control unit is configured to estimate a change in the physiological characteristic of the subject from the determined change in the posture of the torso by evaluating $$PTT(\alpha) = -\frac{1}{m\rho g \sin(\alpha)} \ln\left|1 - \frac{m\rho g l \sin(\alpha)}{mP + n}\right|$$

for each of the first and second postures, where ρ is the density of blood, g is acceleration due to gravity, P is the blood pressure, α is the angle of the torso with respect to the horizontal and m and n are calibration parameters.

In some embodiments, the first BP measurement device is a BP measurement device that can be used to obtain a continuous or semi-continuous measurement of BP.

In some embodiments, the physiological characteristic measured by the first BP measurement device provides a surrogate measurement of BP.

In some embodiments, the physiological characteristic is one or more characteristics of a Photoplethysmogram, PPG, signal, a pulse wave velocity, a pulse arrival time, or a pulse transit time.

In some embodiments, the control unit is further configured to obtain a BP measurement of the subject from a third physiological characteristic measurement by the first BP measurement device and the determined calibration parameter.

In some embodiments, the control unit is further configured to analyse a signal from the first BP measurement device to determine whether the physiological characteristic is stable after obtaining the first physiological characteristic measurement; and configured to obtain the second physiological characteristic measurement if the physiological characteristic is determined to be stable.

According to a fourth aspect, there is provided a method of determining a calibration parameter for a first blood pressure, BP, measurement device, the method comprising obtaining a first physiological characteristic measurement of a subject using the first BP measurement device, wherein the first BP measurement device is for obtaining physiological characteristic measurements of a physiological characteristic of the subject and for determining a BP measurement of the subject from the physiological characteristic measurements using the calibration parameter, wherein the first physiological characteristic measurement is obtained when a torso of the subject is in a first posture; controlling a second BP measurement device to obtain a first BP measurement of the subject when the torso of the subject is in the first posture; obtaining a second physiological characteristic measurement of the subject using the first BP measurement device, wherein the second physiological characteristic measurement is obtained when the torso of the subject is in a second, different, posture; controlling the second BP measurement device to obtain a second BP measurement of the subject when the torso of the subject is in the second posture; and determining a calibration parameter for determining BP measurements from physiological characteristic measurements obtained by the first BP measurement device from an analysis of the first physiological characteristic measurement, the second physiological characteristic measurement, the first BP measurement and the second BP measurement.

In some embodiments, the method further comprises the step of monitoring the posture of the torso of the subject to identify a change in the posture of the torso from the first posture to a second posture; wherein the steps of obtaining the second physiological characteristic measurement and controlling the second BP measurement device to obtain the second BP measurement are performed in response to identifying the change in the posture of the torso to the second posture.

In some embodiments, the method further comprises, after the steps of obtaining the first physiological characteristic measurement and controlling the second BP measurement device to obtain the first BP measurement, the step of causing a change in the posture of the torso of the subject from the first posture to the second posture.

In some embodiments, the step of causing the change in the posture comprises providing an instruction or command to the subject or a care provider for the subject that the posture of the torso of the subject is to be changed.

In some embodiments, the step of causing the change in the posture comprises outputting a control signal to an actuator for a bed or chair associated with the subject to change the angle of the bed or chair.

In some embodiments, the first physiological characteristic measurement and the first BP measurement are obtained at generally the same time.

In some embodiments, the second physiological characteristic measurement and the second BP measurement are obtained at generally the same time.

In some embodiments, the first BP measurement device is a BP measurement device that can be used to obtain a continuous or semi-continuous measurement of BP.

In some embodiments, the physiological characteristic measured by the first BP measurement device provides a surrogate measurement of BP.

In some embodiments, the physiological characteristic is one or more characteristics of a Photoplethysmogram, PPG, signal, a pulse wave velocity, a pulse arrival time, or a pulse transit time.

In some embodiments, the second BP measurement device measures BP using an auscultatory technique, an oscillometric technique, a tonometric technique or a volume-clamp technique.

In some embodiments, the second BP measurement device comprises first and second inflatable cuffs for use on different limbs of the subject, and wherein the control unit is configured to control the second BP measurement device to obtain the first BP measurement of the subject using the first inflatable cuff and to control the second BP measurement device to obtain the second BP measurement of the subject using the second inflatable cuff.

In some embodiments, the method further comprises the step of obtaining a third BP measurement of the subject from a third physiological characteristic measurement by the first BP measurement device and the determined calibration parameter.

In some embodiments, after obtaining the first physiological characteristic measurement, the method comprises analysing a signal from the first BP measurement device to determine whether the physiological characteristic is stable; and obtaining the second physiological characteristic measurement and controlling the second BP measurement device to obtain the second BP measurement if the physiological characteristic is determined to be stable.

According to a fifth aspect, there is provided a computer program product comprising a computer readable medium having computer readable code embodied therein, the computer readable code being configured such that, on execution by a suitable computer or processor, the computer or processor is caused to perform any of the methods according to the fourth aspect described above.

According to a sixth aspect, there is provided an apparatus for determining a calibration parameter for a first blood pressure, BP, measurement device, the apparatus comprising a control unit that is to be coupled to a first BP measurement device that is for obtaining physiological characteristic measurements of a physiological characteristic of a subject and for determining a blood pressure measurement of the subject from the physiological characteristic measurements, and a second BP measurement device that is for obtaining measurements of the blood pressure of the subject, wherein the control unit is configured to obtain a first physiological characteristic measurement of the subject using the first BP measurement device, wherein the first physiological characteristic measurement is obtained when a torso of the subject is in a first posture; control the second BP measurement device to obtain a first BP measurement of the subject when the torso of the subject is in the first posture; obtain a second physiological characteristic measurement of the subject using the first BP measurement device, wherein the second physiological characteristic measurement is obtained when the torso of the subject is in a second, different, posture; control the second BP measurement device to obtain a second BP measurement of the subject when the torso of the subject is in the second posture; and determine a calibration parameter for determining BP measurements from physiological characteristic measurements obtained by the first BP measurement device from an analysis of the first physiological characteristic measurement, the second physiological characteristic measurement, the first BP measurement and the second BP measurement.

In some embodiments, the control unit is further configured to monitor the posture of the torso of the subject to identify a change in the posture of the torso from the first posture to a second posture; and wherein the control unit is configured to obtain the second physiological characteristic measurement and control the second BP measurement device to obtain the second BP measurement in response to identifying the change in the posture of the torso to the second posture.

In some embodiments, the control unit is further configured to cause a change in the posture of the torso of the subject from the first posture to the second posture after obtaining the first physiological characteristic measurement and controlling the second BP measurement device to obtain the first BP measurement.

In some embodiments, the control unit is configured to cause the change in the posture by providing an instruction or command to the subject or a care provider for the subject that the posture of the torso of the subject is to be changed.

In alternative embodiments, the control unit is configured to cause the change in the posture by outputting a control signal to an actuator for a bed or chair associated with the subject to change the angle of the bed or chair.

In some embodiments, the control unit is configured to obtain the first physiological characteristic measurement and the first BP measurement at generally the same time.

In some embodiments, the control unit is configured to obtain the second physiological characteristic measurement and the second BP measurement at generally the same time.

In some embodiments, the first BP measurement device is a BP measurement device that can be used to obtain a continuous or semi-continuous measurement of BP.

In some embodiments, the physiological characteristic measured by the first BP measurement device provides a surrogate measurement of BP.

In some embodiments, the physiological characteristic is one or more characteristics of a Photoplethysmogram, PPG, signal, a pulse wave velocity, a pulse arrival time, or a pulse transit time.

In some embodiments, the second BP measurement device measures BP using an auscultatory technique, an oscillometric technique, a tonometric technique or a volume-clamp technique.

In some embodiments, the second BP measurement device comprises first and second inflatable cuffs for use on different limbs of the subject, and wherein the control unit is configured to control the second BP measurement device to obtain the first BP measurement of the subject using the first inflatable cuff and to control the second BP measurement device to obtain the second BP measurement of the subject using the second inflatable cuff.

In some embodiments, the control unit is configured to obtain a third BP measurement of the subject from a third physiological characteristic measurement by the first BP measurement device and the determined calibration parameter.

In some embodiments, the control unit is configured to analyse a signal from the first BP measurement device to determine whether the physiological characteristic is stable after obtaining the first physiological characteristic measurement; and to obtain the second physiological characteristic measurement and control the second BP measurement device to obtain the second BP measurement if the physiological characteristic is determined to be stable.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1:
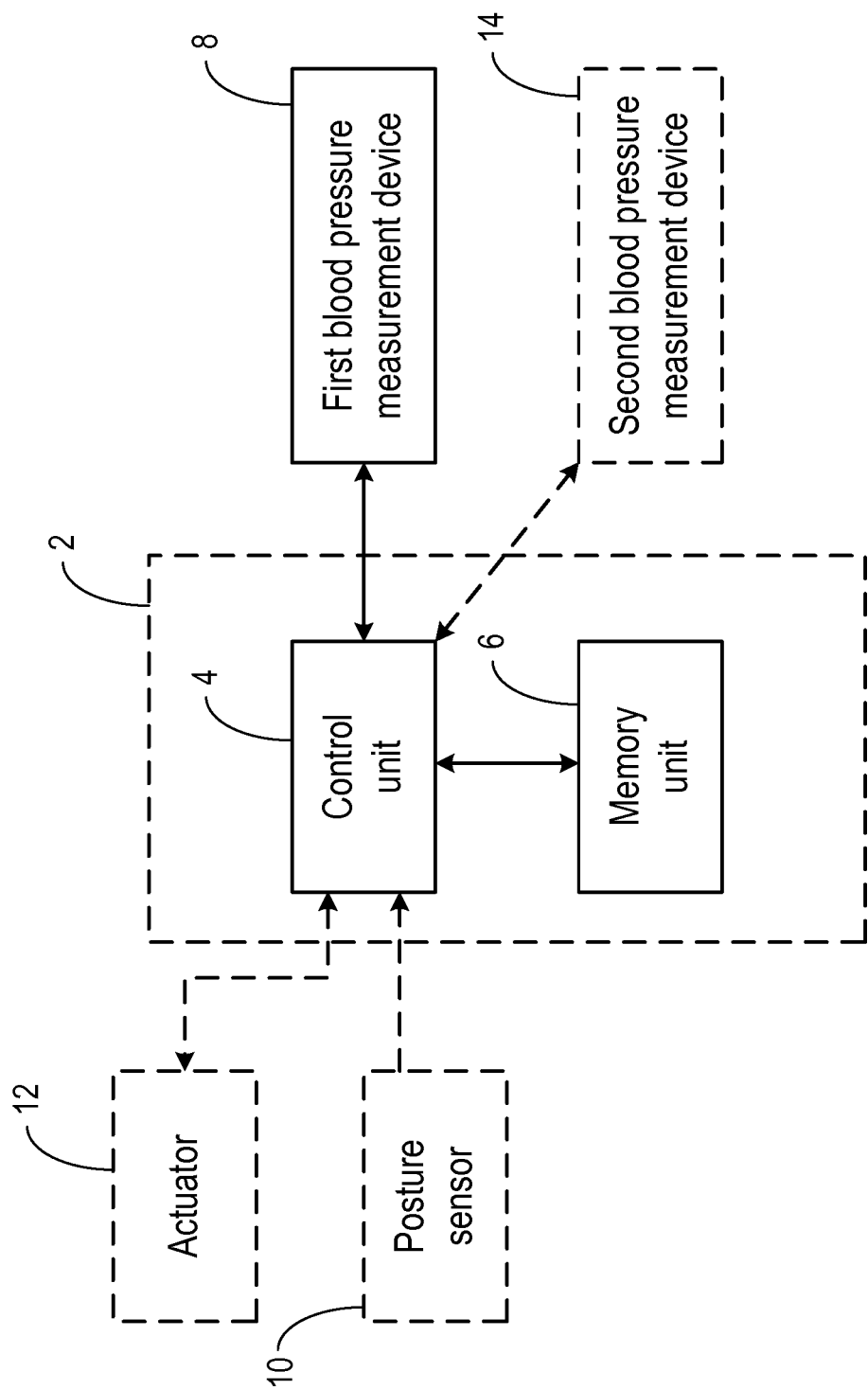
FIG. 1 is a block diagram of a system according to an embodiment that comprises an apparatus according to an embodiment and a first blood pressure measurement device.

As described above, a blood pressure measurement device that uses a 'surrogate' blood pressure measurement technique (i.e. a measurement technique that does not directly measure the blood pressure but infers the blood pressure from measurements of other physiological characteristics) needs to be calibrated using measurements of two different blood pressures, and a reference measurement.

U.S. Pat. No. 8,672,854 indicates that changes in posture of the arm can change the blood pressure, and thus calibration can be performed by using measurements obtained when the arm is in first and second positions.

More generally, it has been shown in the paper "A simplified method for quantifying the subject-specific relationship between blood pressure and carotid-femoral pulse wave velocity" by M. Butlin et al., Engineering in Medicine and Biology Society (EMBC), 2015 37th Annual International Conference of the IEEE, 25-29 Aug. 2015, Milan, pp 5708-5711 that changing from a supine posture to a standing posture produces both a hydrostatic change in the BP (centrally measured from the pulse transit time (PTT) between femoral and carotid artery) and a reaction of the body that can be seen in a change in the blood pressure measured using a brachial cuff (which stays at the level of the heart and is therefore not influenced by hydrostatic changes).

The hydrostatic change was estimated as $\rho gh$ using the density of blood ($\rho=1060$ kg/m$^3$), acceleration due to gravity (g=9.81 m/s), and the height of the fluid column (h), where h was estimated using the linear distance between the supra-sternal notch and the femoral pulse site (positive pressure relative to the brachial diastolic pressure) minus the linear distance between the supra-sternal notch and the carotid pulse site (negative pressure relative to the brachial diastolic pressure). This was divided by two to find the average hydrostatic pressure across the tube length. The calculated hydrostatic pressure in Pascals was converted to mmHg (k=0.0075).

The reaction of the body (leading to the brachial diastolic pressure change) is mainly caused by vessels in the legs that contract to compensate for the reduced blood supply to the brain caused by gravity-induced blood pulling from the head and pooling in the legs. Subjects that might lack this natural reaction are often diagnosed using a so-called "tilt table test". When only the upper body changes posture, e.g. by a change in bed angle, this effect will be a lot smaller and can be neglected.

Thus in embodiments of the invention, measurements of a physiological characteristic that is a surrogate measure of blood pressure are obtained before and after a change in posture of the torso of the subject that changes the height of a location at which the surrogate measure of blood pressure is being measured relative to the heart, and a reference measurement is obtained that is either an estimate of the change in blood pressure caused by the posture change, or measurements of blood pressure obtained using a second blood pressure measurement device (that measures blood pressure more directly (for example using the oscillometric technique or using an arterial line). In some embodiments, for the calibration to be completed in a short length of time (e.g. no more than a few minutes, or even within a small number of breathing cycles), it is possible to induce the change in the blood pressure in the subject by changing the posture of the torso of the subject (or more specifically changing the relative heights of the location at which the surrogate measure of blood pressure is being measured and the heart). For example if the subject is lying on a bed, the angle of the bed can be changed to change the posture and thus induce the blood pressure change. Likewise if the subject is sat on a chair, the angle of the backrest of the chair can be changed to change the posture and thus induce the blood pressure change.

An embodiment of an apparatus 2 for determining a calibration parameter for a first blood pressure measurement device is shown in FIG. 1. The apparatus 2 comprises a control unit 4 and a memory unit 6. The apparatus 2 is shown as part of a system in which the apparatus 2 is coupled (e.g. connected) to a first blood pressure measurement device 8.

The first blood pressure measurement device 8 can measure one or more physiological characteristics of the subject that can be processed (using one or more calibration parameters) to determine the blood pressure of the subject, and the physiological characteristic measurements can be provided to the apparatus 2, and specifically to the control unit 4. It will be understood that the first blood pressure measurement device 8 does not obtain a direct measurement of blood pressure, but instead the first blood pressure measurement device 8 measures a physiological characteristic that is a surrogate for blood pressure, in the sense that blood pressure can be derived from the surrogate physiological characteristic. After calibration, the first blood pressure measurement device 8 may process a physiological characteristic measurement to determine a blood pressure measurement, or the first blood pressure measurement device 8 may provide a subsequent physiological characteristic measurement to the control unit 4, and the control unit 4 can determine the blood pressure measurement from the physiological characteristic measurement and the calibration parameter.

The first blood pressure measurement device 8 preferably measures a physiological characteristic from a central site on the subject so as to provide a surrogate measurement of blood pressure at a central site. It will be understood that a central site corresponds to a core part of the body of the subject, such as the torso, abdomen, chest or neck, rather than a peripheral part of the body, such as the limbs.

The control unit 4 can control the taking or triggering of physiological characteristic measurements by the first blood pressure measurement device 8.

The apparatus 2 can be coupled to the first blood pressure measurement device 8 using any suitable means or type of connection, for example using wires, or using a wireless connection (e.g. a short or long range communication protocol such as Bluetooth, Wi-Fi, 3G or 4G cellular communications, etc.).

The first blood pressure measurement device 8 is a type of measurement device that requires regular calibration (e.g. of the order of a few minutes, every hour, or when a physiological characteristic changes significantly (e.g. by more than a threshold amount)) in order to provide accurate, or sufficiently accurate, measurements of blood pressure from measurements of a (non-blood pressure) physiological characteristic. A mathematical function is used to relate the surrogate physiological characteristic measurement to blood pressure, and this function includes one or more factors and/or constants. The values of these factors and/or constants are determined in the calibration procedure. These factors and/or constants are referred to herein as "calibration parameters". Thus the calibration of the first blood pressure measurement device 8 is provided by determining (values for) one or more calibration parameters, that are used as part of the mathematical function to convert the physiological characteristic measurement obtained by the device 8 to the subject's blood pressure. After calibration, the first blood pressure measurement device 8 is preferably able to provide a continuous or near continuous (e.g. every second, every minute, or every heart beat) measurement of blood pressure, and also preferably obtains the measurement non-invasively.

For example, the surrogate physiological characteristic measurement used to determine blood pressure can be a pulse arrival time (PAT) measurement, which makes use of the time difference between the R-peak in an electrocardiogram (ECG) signal and the time of arrival of a pulse in a finger, which can be measured using a photoplethysmography (PPG) sensor or an accelerometer.

As another, more preferred, example, the first blood pressure measurement device 8 can use pulse wave velocity (PWV) as the surrogate physiological characteristic measurement that is used to determine blood pressure. PWV can be measured as the time difference between the arrival of a pulse at two different locations in the body, e.g. in a femoral artery and in the carotid artery, which is known as the Pulse Transit Time (PTT). The PWV can be measured using a sensor at each location (i.e. at the top of the leg for the femoral artery and at the neck for the carotid artery) with the PWV being given by the distance between the measurement sites divided by the PTT. The sensor for each location can be, for example, a photoplethysmography (PPG) sensor, a remote radar sensor, a camera, an accelerometer or a gyroscope. In the case of a remote radar sensor or camera, a single radar sensor or camera can be used to measure the arrival of a pulse at multiple sites on the body (e.g. the carotid artery and femoral artery) and thus pulse transit times through suitable processing of the obtained radar measurements or camera images. However the use of accelerometers for measuring the PWV is advantageous as they are cheaper and consume less power than PPG sensors and the peaks in the signal are 'sharper' and thus easier to identify. In addition, in the embodiments where a posture sensor is used to determine or monitor the posture of the torso of the subject, the accelerometers, gyroscopes, radar sensor or camera in the first blood pressure measurement device 8 can be used for this purpose, i.e. they can be used both to measure the pulse and the posture of the torso.

Figure 2:
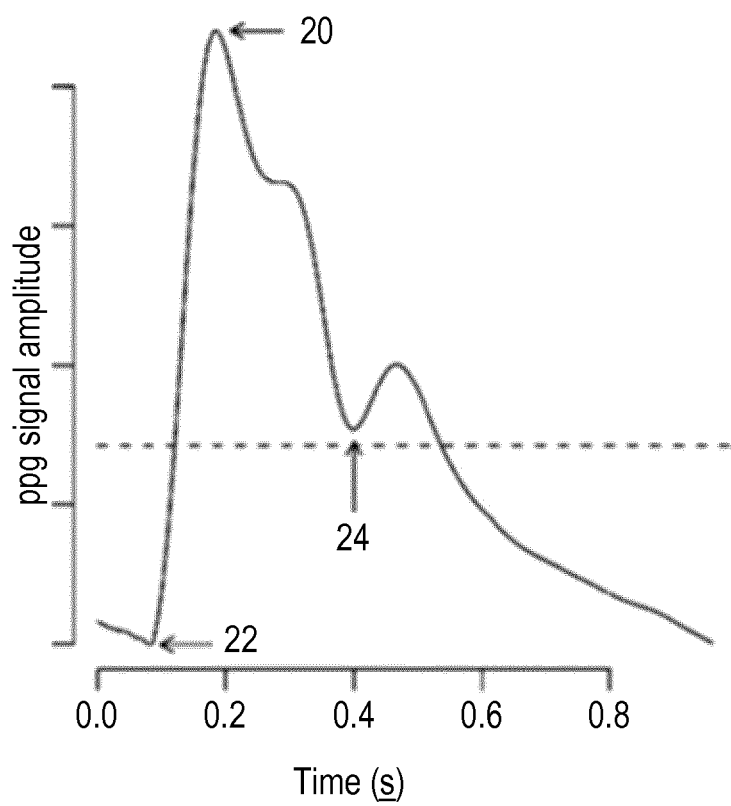
FIG. 2 is a graph illustrating an exemplary photoplethysmograph (PPG) signal.

Alternatively the physiological characteristic can comprise various signal characteristics that can be determined from a PPG waveform (signal) and blood pressure can be obtained from a combination of features in the PPG signal. An exemplary PPG signal is shown in FIG. 2, and the features that can be used to determine blood pressure include any one or more of the amplitude of the highest peak 20 in the PPG signal, the DC value of the PPG signal, the slope or gradient of a line connecting the foot 22 of the pulse with the peak 20 of the pulse, or the location (in time) of the dicrotic notch 24.

It will be appreciated that a PPG signal can be obtained by a light sensor that is in contact with the skin of the subject, or by analysis of video images obtained by a camera or other video or image sensor that is remote from the body of the subject. Techniques for extracting a PPG signal from a video sequence are known in the art and are not described herein.

The above types of blood pressure measurement devices and their construction and method of operation will be well known to those skilled in the art, and thus detailed explanations are not provided in this document.

As noted above, the apparatus 2 determines a calibration parameter for the first blood pressure measurement device 8 by obtaining measurements of the physiological characteristic measured by the first blood pressure measurement device 8 in two different postures of the torso of the subject. Therefore, in some embodiments, the apparatus 2 can further comprise, or be connected to, a posture sensor 10 that obtains measurements of the posture of the torso of the subject, or measurements that can be processed to determine the posture of the torso of the subject.

For example, the posture sensor 10 can be one or more accelerometers or gyroscopes that are located on or worn by the subject and that are in a known orientation with respect to the subject, and the posture of the torso of the subject can be determined by determining the direction of gravity (i.e. representing the vertical direction in the earth's frame of reference) in the acceleration measurements or the rotation (given by the gyroscope measurements) from a known orientation/posture. Alternatively, the posture sensor 10 can comprise a camera or radar sensor whose images or measurements can be processed to identify the position or posture of the torso of the subject.

As noted above, where the first blood pressure measurement device 8 comprises two or more accelerometers or gyroscopes that measure the arrival of a pulse at the location of the accelerometer or gyroscope, one or both of these accelerometers or gyroscopes can act as the posture sensor 10 and thus no separate accelerometer or gyroscope is required for use with the apparatus 2. Thus in these embodiments, no additional posture sensor 10 is required in the apparatus 2.

Alternatively, where the apparatus 2 is to be used to measure the blood pressure of a subject that is lying on a bed or sat in a chair (e.g. in a hospital, ICU or OR setting), the posture sensor 10 can be a sensor on or in the bed or chair that indicates the tilt angle of the bed or chair. This tilt angle can be the angle of the entire bed or chair or the angle of a part of the bed or chair that supports the torso of the subject (e.g. an angle of an upper portion of the bed or backrest of the chair).

In another alternative, the posture sensor 10 can comprise a camera or other video or image sensor that obtains images or a video sequence of the subject, and these images or video sequence can be processed by the control unit 4 or other processing unit to determine the posture of the subject. In some embodiments, a camera or other video or image sensor can be used in combination with an accelerometer or other body-worn posture sensor 10 in order to verify that the subject is in the posture suggested by the body-worn sensor 10. Where the first blood pressure measurement device 8 comprises a camera or radar sensor that is used to measure pulse arrival time at one or more locations of the body (or another physiological characteristic that is a surrogate for blood pressure), the radar measurements or camera images can also be processed to determine the posture of the subject. Thus in these embodiments, no additional posture sensor 10 is required in the apparatus 2.

Those skilled in the art will be aware of other types of sensor that can be used to measure or observe the posture of the subject.

In some embodiments of the invention, to reduce the time required for the calibration procedure and/or avoid the subject having to take any specific action, the apparatus 2 can induce or cause the torso of the subject to change posture. In particular, where the apparatus 2 is used to measure the blood pressure of a subject that is lying on a bed or sat on a chair, in which case the control unit 4 can be connected to an actuator 12 for the bed or chair that can change the angle of the bed or chair (e.g. the angle of the whole bed or chair or a part supporting the torso of the subject). The actuator 12 may be a motor, piston, or any other suitable type of actuator that can be operated in response to a control signal from the control unit 4.

As noted above, in some embodiments the apparatus 2 uses measurements of blood pressure by the second blood pressure measurement device 14 to determine one or more calibration parameters that relate the measurements of the physiological characteristic by the first blood pressure measurement device 8 to blood pressure.

Thus, in some embodiments the apparatus 2 can also be coupled to a second blood pressure measurement device 14. The second blood pressure measurement device 14 measures the blood pressure of the subject, and the measurements of blood pressure can be provided to the control unit 4. The control unit 4 can control the taking or triggering of blood pressure measurements by the second blood pressure measurement device 14.

The apparatus 2 can be coupled to the second blood pressure measurement device 14 using any suitable means or type of connection, for example using wires, or using a wireless connection (e.g. a short or long range communication protocol such as Bluetooth, Wi-Fi, 3G or 4G cellular communications, etc.).

The second blood pressure measurement device 14 is a different type of blood pressure measurement device to the first blood pressure measurement device 8 and measures blood pressure using a different technique to the first blood pressure measurement device 8.

In contrast to the first blood pressure measurement device 8, the second blood pressure measurement device 14 is a type of measurement device that does not require regular calibration using measurements from another blood pressure measurement device in order to provide accurate, or sufficiently accurate, measurements of blood pressure. The second blood pressure measurement device 14 is typically a device that can be used to obtain intermittent measurements of blood pressure, although one that does so with relatively high accuracy. The second blood pressure measurement device 14 preferably uses a so-called 'direct' measurement to determine the blood pressure, although the second blood pressure measurement device 14 is preferably not a device that obtains the measurement invasively. For example, the second blood pressure measurement device 14 can comprise an inflatable cuff and a sound sensor that is used to detect Korotkoff sounds as the cuff is inflated and/or deflated (this type of device uses the auscultatory technique).

Alternatively, the second blood pressure measurement device 14 can use the oscillometric technique in which the device 14 comprises an inflatable cuff and a pressure sensor and the pressure in the inflatable cuff is measured and the oscillations in the pressure analysed to determine the blood pressure.

As another alternative, the second blood pressure measurement device 14 can be an invasive device that is implanted in the body, for example in an artery, and that directly measures the blood pressure. It will be appreciated that although these types of devices can provide continuous or semi-continuous measurements of blood pressure, they may be subject to battery constraints, and thus the implanted device may be used in a power saving mode to maximise the battery life and thus may only be used to obtain the blood pressure measurements required for calibrating the first blood pressure measurement device 8.

In some embodiments, the second blood pressure measurement device 14 can be a type of device that is self-calibrating (i.e. a device that does require calibrating to obtain accurate measurements, but does not require the use of another blood pressure measurement device to do so). Examples include volume-clamp based blood pressure measurement devices, which use a cuff on a finger or other peripheral part of the body of the subject and a PPG sensor. It will be appreciated that although these types of devices can provide continuous or semi-continuous measurements of blood pressure, they may cause discomfort to the subject by the continuous pressure on the finger, and thus the volume-clamp device may be used in a 'comfort' mode to minimise the patient discomfort and thus may only be used to obtain the blood pressure measurements required for calibrating the first blood pressure measurement device 8, while the cuff may be deflated the rest of the time.

In other embodiments, the second blood pressure measurement device 14 can be based on applanation tonometry.

These types of blood pressure measurement devices and their construction and method of operation will be well known to those skilled in the art, and thus detailed explanations are not provided in this document.

The control unit 4 controls the operation of the apparatus 2, for example controlling the triggering of the collection of physiological characteristic measurements by the first blood pressure measurement device 8 and the processing to determine the calibration parameters for the first blood pressure measurement device 8. The control unit 4 can also control other functions and operations of the apparatus 2. The control unit 4 can be implemented in numerous ways, with software and/or hardware, to perform the various functions required. The control unit 4 may comprise one or more microprocessors that may be programmed using software to perform the required functions. The control unit 4 may be implemented as a combination of dedicated hardware to perform some functions and a processor (e.g., one or more programmed microprocessors and associated circuitry) to perform other functions. Examples of processing components that may be employed in various embodiments of the present disclosure include, but are not limited to, conventional microprocessors, application specific integrated circuits (ASICs), and field-programmable gate arrays (FPGAs).

In various implementations, the control unit 4 may be associated with one or more storage media, shown as memory unit 6 in FIG. 1. The memory unit 6 can be part of the control unit 4, or it can be a separate component in the apparatus 2 that is connected to the control unit 4. The memory unit 6 can comprise any suitable or desired type of volatile or non-volatile computer memory such as RAM, PROM, EPROM, and EEPROM. The memory unit 6 can be used for storing computer program code that can be executed by the control unit 4 to perform the method described herein. The memory unit 6 can also be used to store signals or measurements from the first blood pressure measurement device 8, and/or information relating to the calibration of the first blood pressure measurement device 8.

In some embodiments, the first blood pressure measurement device 8 and the other potential components (i.e. the posture sensor 10, the actuator 12 and the second blood pressure measurement device 14) are separate from the apparatus 2 (i.e. they are separate devices). As noted above, the apparatus 2 can be coupled to the first blood pressure measurement device 8 wirelessly or using wires. In these embodiments the apparatus 2 can be implemented by a personal electronic device such as a smartphone, tablet computer, laptop computer or desktop computer, or electronic device present in a clinical environment, such as a bedside monitor, patient monitoring system, sensor array, etc. In some embodiments, the apparatus 2 can be implemented in a computer or server that is remote from the first blood pressure measurement device 8 (e.g. the apparatus 2 could be located in the cloud, i.e. accessible via the Internet).

In other embodiments, the first blood pressure measurement device 8 is part of (i.e. integral with) the apparatus 2, and the apparatus 2 can be coupled (e.g. using wires or wirelessly).

It will be appreciated that FIG. 1 only shows the components required to illustrate various embodiments of the apparatus 2, and in a practical implementation the apparatus 2 will comprise additional components to those shown. For example, the apparatus 2 may comprise a battery or other power supply for powering the apparatus 2, a communication module for enabling the blood pressure measurements or determined calibration parameters for the blood pressure measurements by the first blood pressure measurement device 8 to be communicated to another device, e.g. a remote computer (e.g. that stores health parameter measurement records for the subject) and/or one or more user interface components that allow the subject or another user to interact and control the apparatus 2. As an example, the one or more user interface components could comprise a switch, a button or other control means for activating and deactivating the apparatus 2 and/or calibration parameter determination process. The user interface components can also or alternatively comprise a display or other visual indicator for providing information to the subject and/or other user about the operation of the apparatus 2, including displaying information on a determined blood pressure.

In some embodiments, the apparatus 2 and first blood pressure measurement device 8 (and optional posture sensor 10 and/or second blood pressure measurement device 14) can be integrated into an item of clothing, for example a shirt or jumper.

Figure 3:
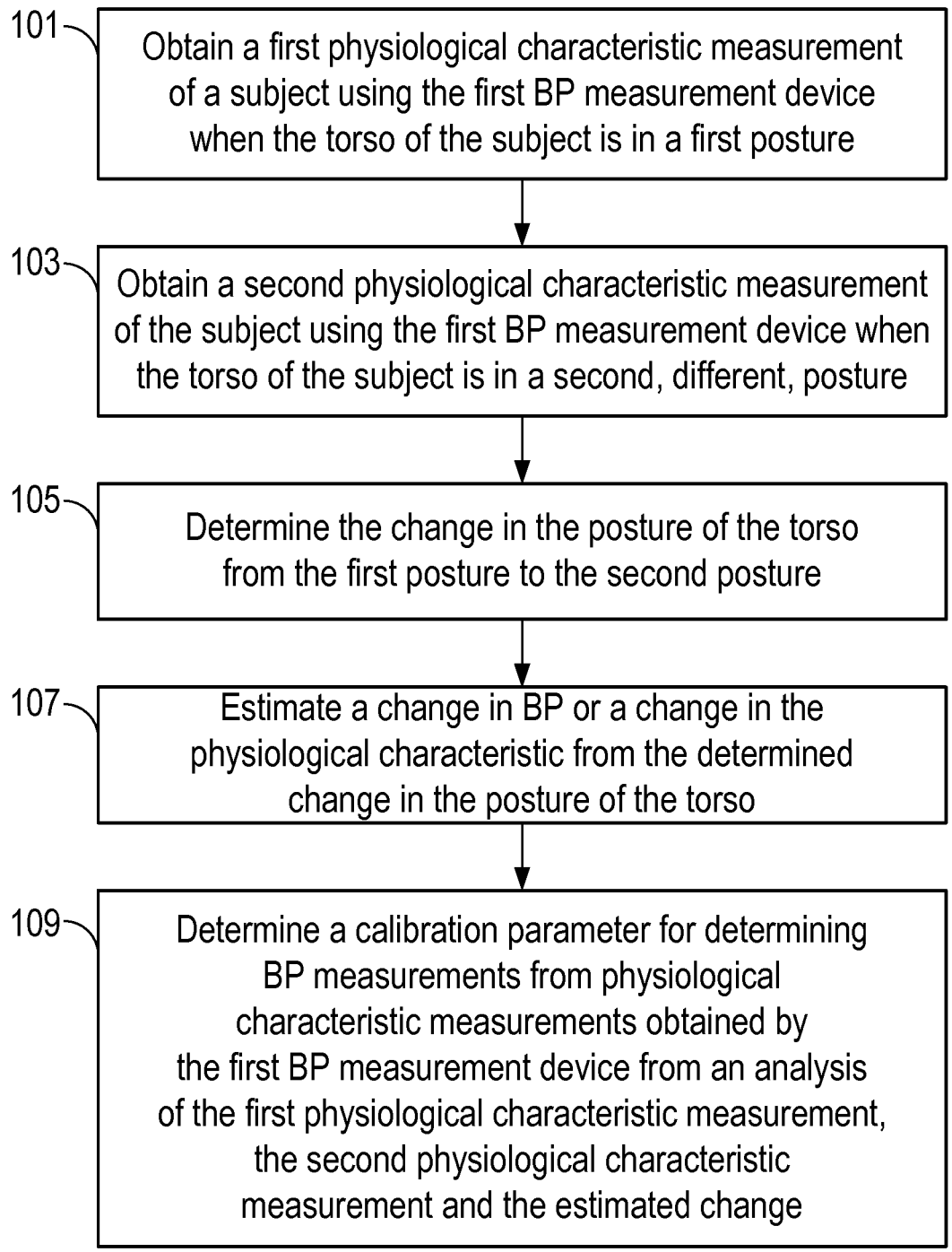
FIG. 3 is a flow chart illustrating a method according to an aspect.

The flow chart in FIG. 3 illustrates a method of determining a calibration parameter for the first blood pressure measurement device 8 in accordance with an aspect. This method can be implemented or performed by the control unit 4. Since the first blood pressure measurement device 8 is to be used to continuously or semi-continuously measure a physiological characteristic in the subject and requires calibration before sufficiently accurate blood pressure measurements can be obtained from those physiological characteristic measurements, the method of FIG. 3 can be performed when the first blood pressure measurement device 8 is first activated. The method of FIG. 3 can also be performed periodically in order to recalibrate the first blood pressure measurement device 8 (e.g. every few minutes or every hour, etc.) or as required (e.g. when the physiological characteristic being measured by the first blood pressure measurement device 8 has changed by more than a threshold amount).

In step 101, a measurement of the surrogate physiological characteristic of the subject is obtained using the first blood pressure measurement device 8. This step may comprise the control unit 4 outputting a suitable control or trigger signal to the first blood pressure measurement device 8 to cause the first blood pressure measurement device 8 to perform a physiological characteristic measurement, or, since the first blood pressure measurement device 8 may be continuously measuring the physiological characteristic, this step may comprise the control unit 4 receiving or obtaining the most recent physiological characteristic measurement from the first blood pressure measurement device 8. This physiological characteristic measurement is referred to as the 'first' physiological characteristic measurement and is obtained when the torso of the subject is in a 'first' posture. This posture can be lying down (face up, face down or lying on the side), e.g. with the torso at an angle $\alpha$ of 0° with respect to a horizontal plane, sitting upright (e.g. with the torso at an angle $\alpha$ of 90° with respect to the horizontal plane), or lying an angle between a flat and upright posture (e.g. with the torso at an angle $\alpha$ between 0° and 90° with respect to the horizontal plane). It will be appreciated that, for the purposes of this invention, the posture of the torso corresponds to the angle of the longitudinal axis of the torso with respect to the earth's reference frame (where the angle can be measured with respect to a vertical direction, e.g. corresponding to the direction of gravity, or a horizontal direction, e.g. corresponding to a direction that is perpendicular to the direction of gravity).

As noted above, in preferred embodiments the physiological characteristic is measured at a central site on the body in order to derive a central measurement of the blood pressure. For example the physiological characteristic can be the pulse wave velocity (PWV) which is derived from the pulse transit time (PTT), which is itself determined by measuring the arrival of a pulse at two different locations in the body of the subject (e.g. in the femoral artery and carotid artery). Thus step 101 can comprise obtaining a measurement of the arrival time of a pulse at two locations and deriving the PTT and PWV therefrom.

Next, in step 103, which takes place when the torso of the subject is in a different (second) posture to that used in step 101 (i.e. the torso is at a different angle in step 103 than in step 101), the control unit 4 obtains another measurement of the physiological characteristic using the first blood pressure measurement device 8. This physiological characteristic measurement is referred to as the 'second' physiological characteristic measurement. As with step 101, since the first physiological characteristic measurement device 8 is monitoring the physiological characteristic continuously or semi-continuously, step 103 may comprise the control unit 4 obtaining a current physiological characteristic measurement from the first blood pressure measurement device 8, rather than the control unit 4 explicitly requesting a physiological characteristic measurement at that time. Alternatively however, this step can comprise the control unit 4 controlling the first blood pressure measurement device 8 to make a measurement of the physiological characteristic.

It will be appreciated that for the calibration parameter to be determined, the difference in the postures (angle) between steps 101 and 103 should be sufficient for there to be a change in the blood pressure of the subject. Thus, it is not necessarily required for the torso of the subject to change between a flat lying posture and an upright posture (or vice versa). Typically an angular change of the torso of 10° to 20° from a flat lying positing towards an upright posture is sufficient to generate a blood pressure difference larger than the typical error spread of 4 to 8 mmHg for oscillometric BP measurement devices, and thus the posture change between steps 101 and 103 can be of the order of 10° or more.

In step 105, the control unit 4 determines the change in the posture of the torso from the first posture to the second posture. This step can comprise analysing the signal output by posture sensor 10 (or accelerometer in the first blood pressure measurement device 8 in the preferred embodiment) over time to identify the change in posture. In some embodiments, the change in posture determined in step 105 can be determined as the angle by which the torso has changed. In the case of an accelerometer, it will be appreciated that the angle can be determined as the angle by which the direction of gravity has changed in the accelerometer's frame of reference.

It will be appreciated that in some embodiments step 105 can be performed before step 103 in order for the control unit 4 to determine that a posture change has occurred before triggering or initiating the second measurement of the physiological characteristic in step 103. This may be useful where the posture change is not directly caused by the control unit 4 (e.g. where the control unit 4 simply waits for the subject to change their posture naturally or where the control unit provides a prompt or instruction to the subject to change their posture). In other embodiments, particularly embodiments where the control unit 4 directly causes a change in posture (e.g. by causing the actuation of a bed or chair), steps 103 and 105 can be performed in the order shown in FIG. 3.

After determining the change in posture in step 105, the control unit 4 estimates a change in the blood pressure or the physiological characteristic of the subject caused by the posture change (step 107). In some embodiments, the control unit 4 uses the posture change determined in step 105 to determine the change in height of a location at which the physiological characteristic is being measured with respect to the heart, and estimates the change in blood pressure from the determined change in height. In particular, the control unit 4 estimates the hydrostatic pressure change caused by the change in posture. As known, a hydrostatic pressure change shows itself in the blood pressure as a reduction in the blood pressure at measurement sites that are elevated relative to the heart level and an increase in the blood pressure at measurement sites that are lowered relative to the heart level. In alternative embodiments, in step 107 the control unit 4 uses the posture change determined in step 105 to determine the change in the physiological characteristic that is used as a surrogate measure of blood pressure. For example the control unit 4 can determine a change in pulse transit time (PTT) caused by the posture change. Examples of both embodiments are described below.

In order to get an estimation of the blood pressure change due to a posture change, in some embodiments, an estimation is made for the blood pressure change due to the body response and this estimation is added to a calculated or estimated hydrostatic pressure change. In other embodiments, the estimated blood pressure change only incorporates the hydrostatic effect and neglects the effect of the change in blood pressure due to a body response. This could be applied to situations where the second physiological characteristic measurement is performed before the body has responded to the change in posture and to situations where only the upper body (and not the legs) changes angle, such as in a bed where the legs stay horizontal while the upper part of the bed changes angle. Two specific embodiments where this is applied are given in the next two paragraphs.

Figure 4:
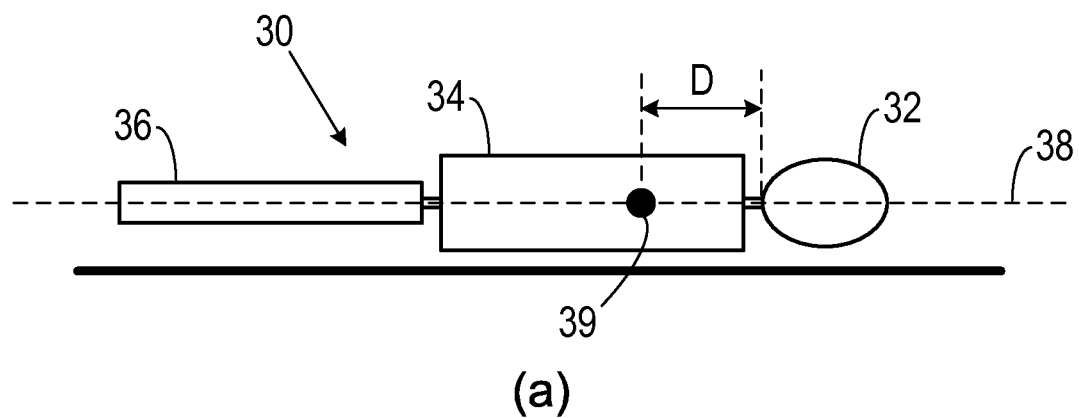
FIG. 4 is an illustration of the change in height relative to the heart for a blood pressure measurement site due to a change in posture of the torso.
Figure 4:
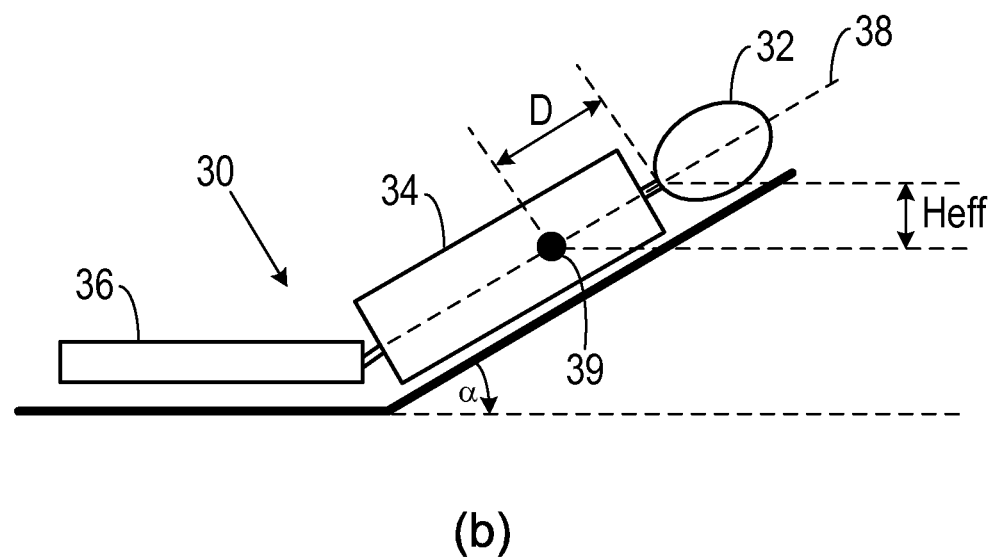

In the first embodiment, the surrogate blood pressure measurement is based on only one sensor on a single location on the body. For example, the features in the PPG signal of a sensor in the neck, at a distance D from the heart, are used. This is illustrated in FIG. 4. FIG. 4 shows a subject 30 in two different postures, lying flat in FIG. 4(a) and lying with their torso (upper body) at an angle α in FIG. 4(b). The subject 30 is shown in block form with a head 32, torso 34 and legs 36. The central axis of the torso 34 (also known as the longitudinal axis) is shown by dashed line 38. The heart of the subject is shown as point 39, and there is a distance D between the heart and the point at which the PPG signal is measured in the neck. Thus when the subject 30 is lying flat in FIG. 4(a) there is no difference in the height of the location of the sensor and the heart, but there is a height difference $H_{\textit{eff}}=D.(\sin \alpha)$ between the sensor location and the heart when the torso 34 is at an angle α with respect to the horizontal plane. Thus, the hydrostatic pressure change when changing from the lying posture in FIG. 4(a) to posture at angle α in FIG. 4(b) is given by $\rho g H_{\textit{eff}}$. When changing posture from angle $\alpha=\alpha_1$ to angle $\alpha=\alpha_2$, the hydrostatic pressure change is caused by a change from $H_{\textit{eff}}(\alpha_1)$ to $H_{\textit{eff}}(\alpha_2)$ and is thus equal to $\rho g D.(\sin \alpha_1 - \sin \alpha_2)$. Therefore it can be seen that, a change in the posture of the torso will lead to a predictable blood pressure change, and this blood pressure change can be used with the measurements of the physiological characteristic obtained in steps 101 and 103 to determine the calibration parameters.

Figure 5:
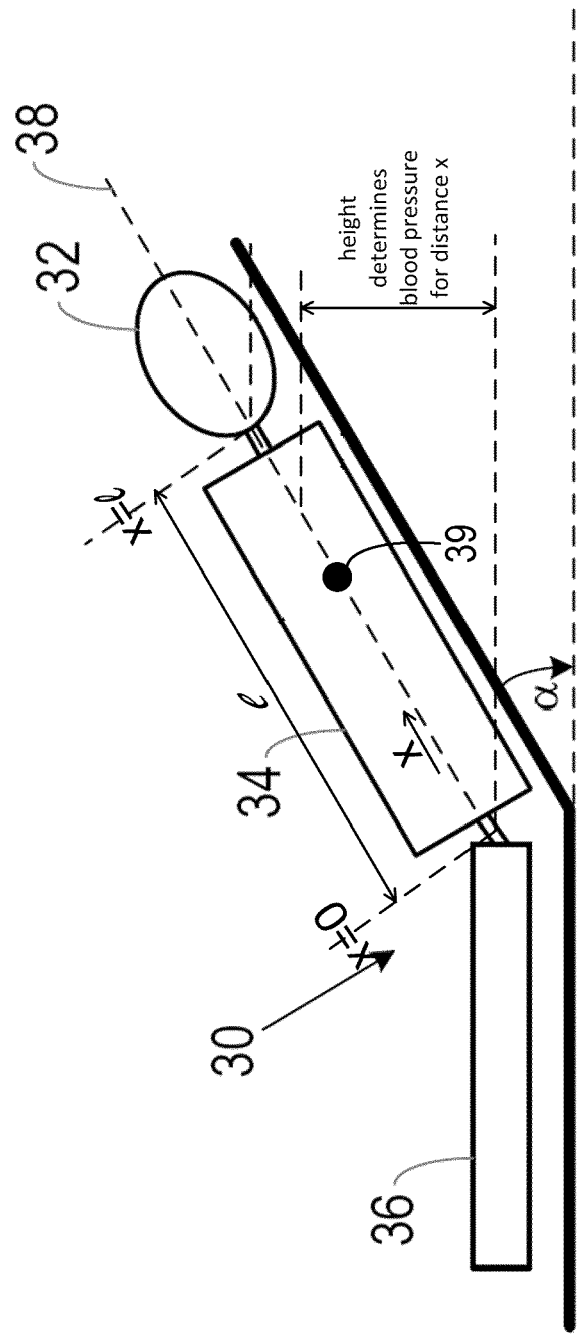
FIG. 5 is an illustration of the change in blood pressure due to changes in posture of the torso.

In the second embodiment, where a change in the physiological characteristic due to the posture change is estimated, the surrogate blood pressure measurement (physiological characteristic measurement) can be the pulse transit time of the carotid-femoral path. A change in angle α affects the blood pressure everywhere along the carotid-femoral path in a different way. Therefore the local blood pressure should be considered to determine the pulse wave velocity PWV. In a first approximation, it is assumed that the arterial path from the carotid to the femoral artery is straight, parallel to the central axis of the torso 34 (also known as the longitudinal axis, shown as dashed line 38 in FIG. 5), and has length l. Length l is a subject-dependent parameter (i.e. different for different subjects) that may have been measured or estimated and input into the apparatus 2 during a set up phase. Coordinate x runs along the longitudinal axis 38 of the torso and starts at zero at the pulse location of the femoral artery. Blood pressure P is a function of x and α:

$$P(x,\alpha)=P_0-\rho g x.\sin(\alpha) \qquad (1)$$

where $P_0$ is the blood pressure at x=0. Next, the pulse wave velocity is approximated to be linearly related to the blood pressure:

$$\text{PWV}=mP+n \qquad (2)$$

where m and n are the calibration parameters that should be determined from the calibration procedure. Substituting equation (1) in equation (2) gives:

$$\text{PWV}=m(P_0-\rho g x.\sin(\alpha))+n \qquad (3)$$

The pulse transit time PTT is the integral of the PWV over the distance, thus $$PTT(\alpha) = \int_0^l \frac{dx}{PWV(P(\alpha))} \quad (4)$$

Substituting equation (3) in equation (4) finally gives the result:

$$PTT(\alpha) = -\frac{1}{m\varrho g \sin(\alpha)} \ln\left|1 - \frac{m\varrho g l \sin(\alpha)}{mP + n}\right| \quad (5)$$

Thus, PTT can be determined in the first and second postures (i.e. with first and second values of α), and thus when PTT and a are known before the posture change and after the posture change, calibration parameters m and n can be determined in step 107.

Figure 6A:
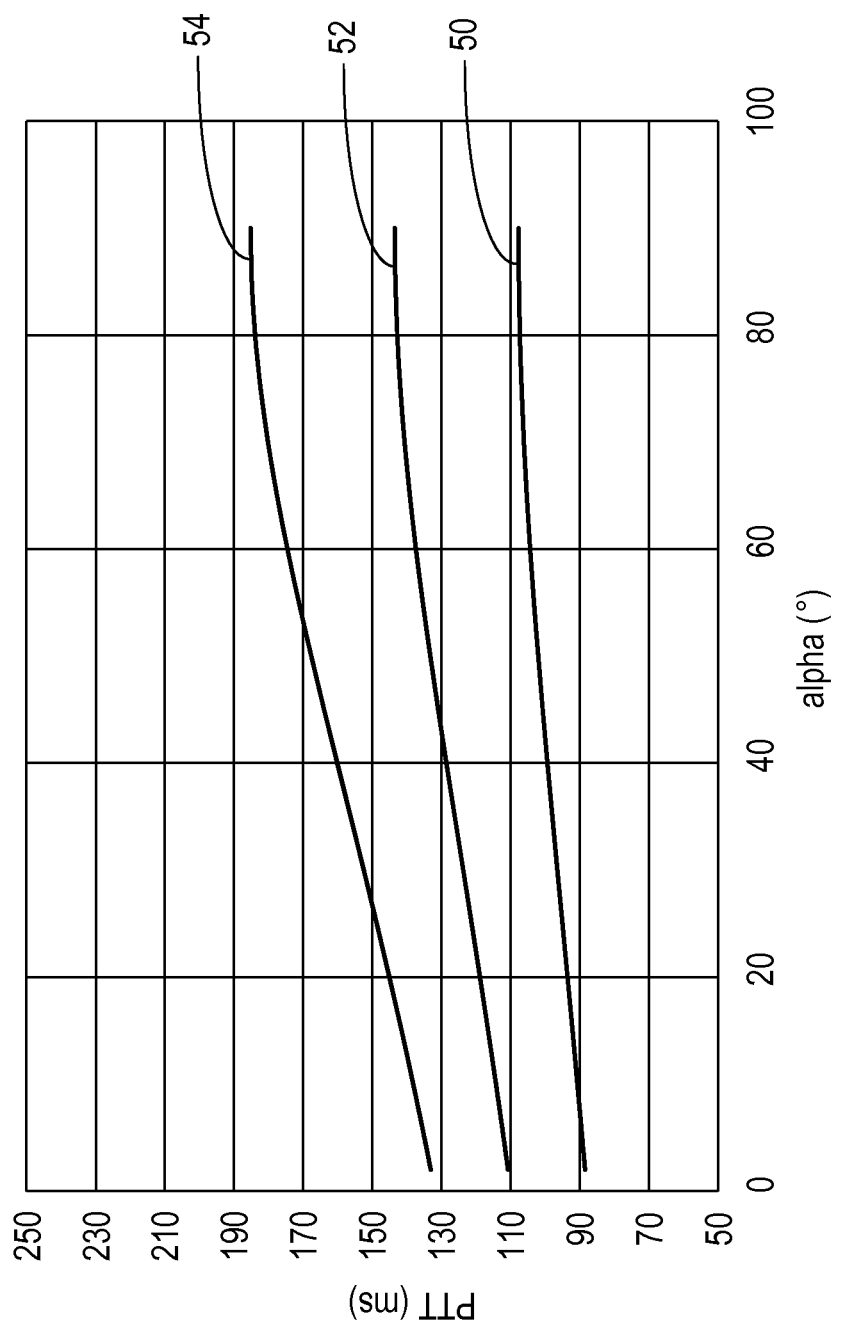
FIG. 6 shows how pulse transit time varies as a function of the angle of the torso.
Figure 6B:
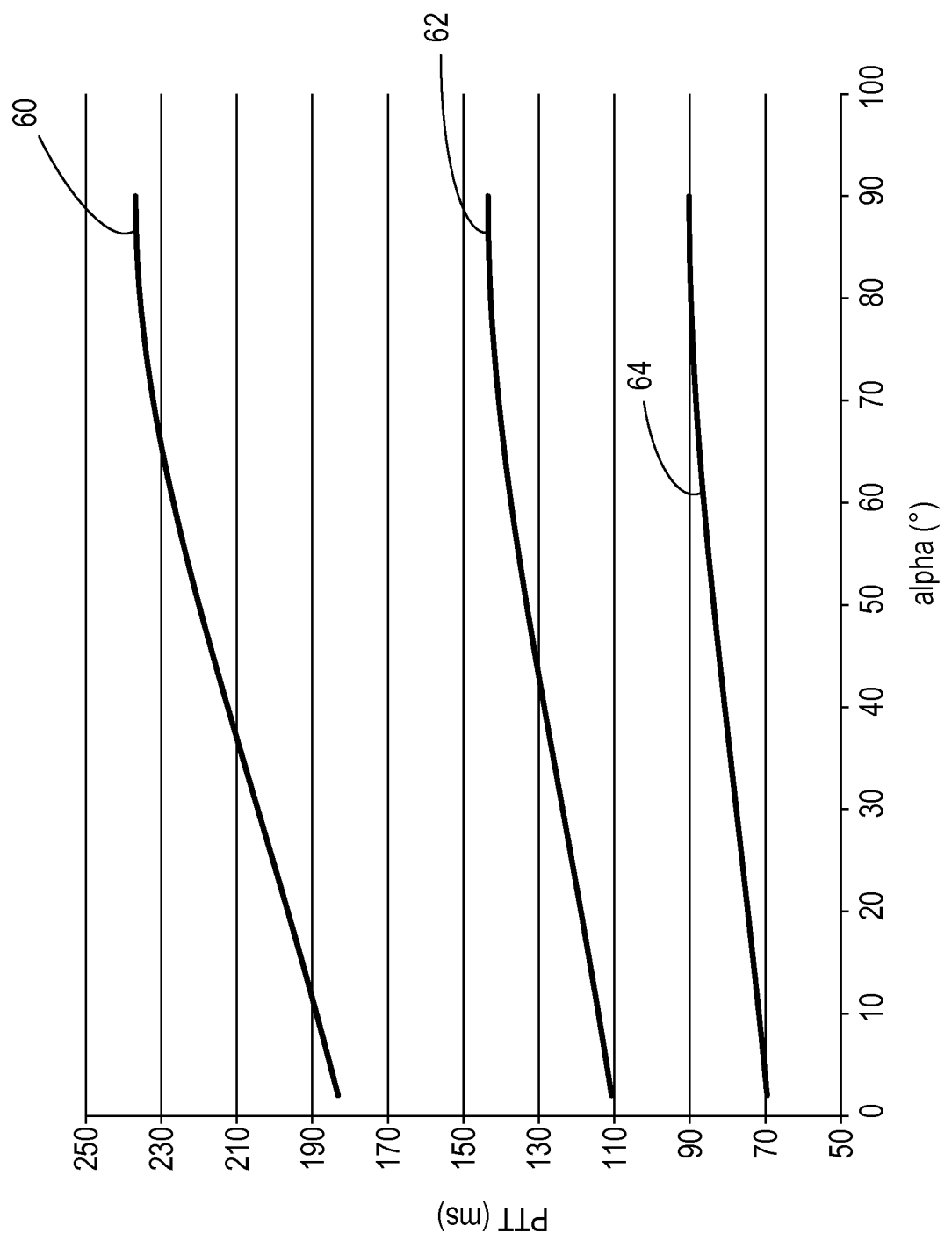
Figure 6C:
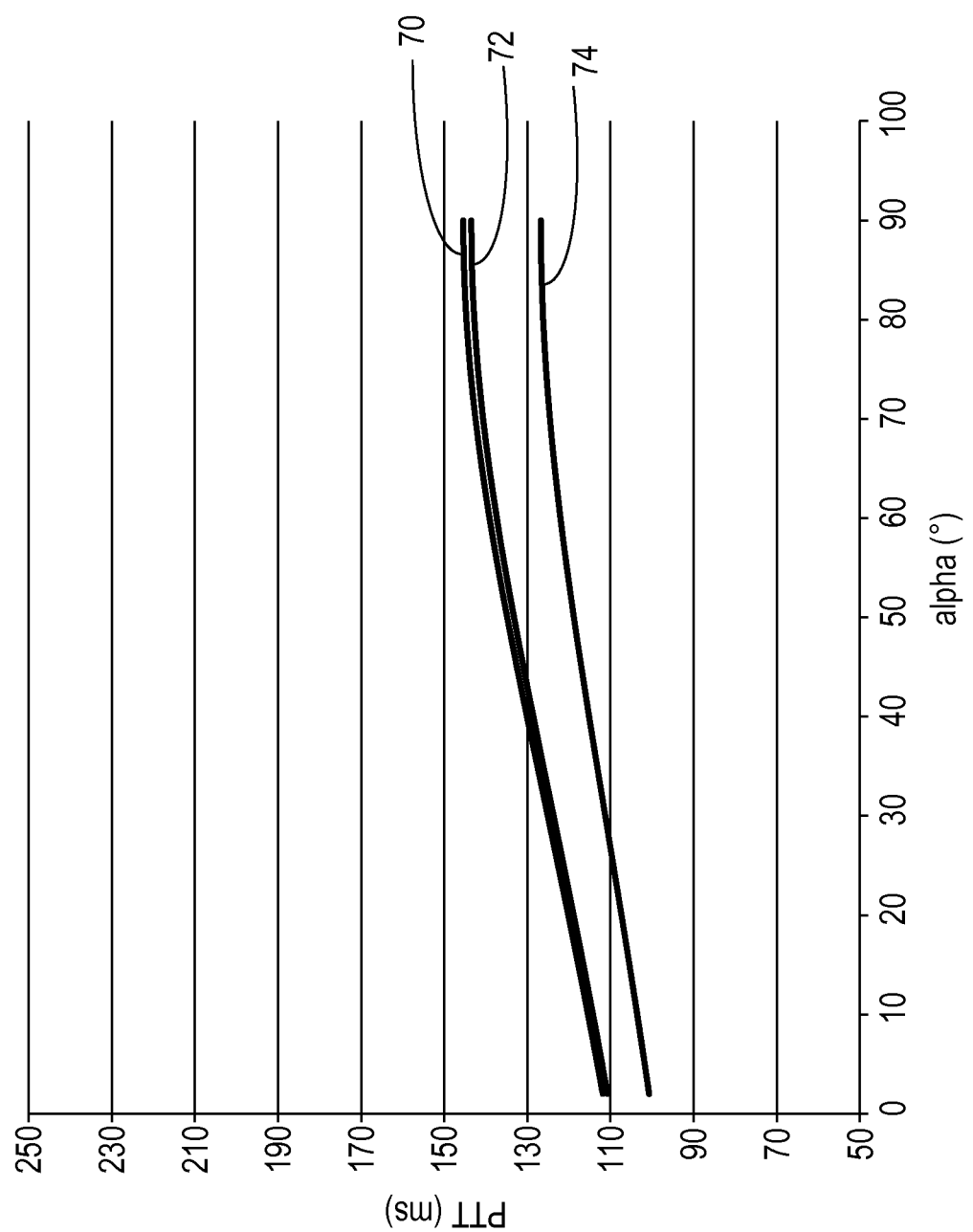

FIG. 6 shows how PTT behaves as a function of a for several values of l (and thus shows the difference between subject with a long torso and those with a short torso) in FIG. 6(*a*), several values of m in FIG. 6(*b*) and several values of n in FIG. 6(*c*). m is 0.05 m/s/mmHg in FIGS. 6(*a*) and 6(*c*), n is 0.05 m/s in FIGS. 6(*a*) and 6(*b*), and l is 50 cm in FIGS. 6(*b*) and 6(*c*). In FIG. 6(*a*) lines for three different values of l are shown, l=40 cm (line 50), l=50 cm (line 52) and l=60 cm (line 54). In FIG. 6(*b*) lines for three different values of m are shown, m=0.02 m/s/mmHg (line 60), m=0.05 m/s/mmHg (line 62) and m=0.08 m/s/mmHg (line 64). In FIG. 6(*c*) lines for three different values of n are shown, n=0.005 m/s (line 70), n=0.05 m/s (line 72) and n=0.5 m/s (line 74).

Thus, as explained by means of the two examples in the previous two paragraphs, after step 107, the control unit 4 determines one or more calibration parameters for the first blood pressure measurement device 8 from an analysis of the first physiological characteristic measurement, the second physiological characteristic measurement, and the estimated change in blood pressure or change in the physiological characteristic due to the posture change (step 109). That is, the control unit 4 determines one or more calibration parameters that are to be applied to subsequent physiological characteristic measurements by the first blood pressure measurement device 8 in order to provide accurate (or sufficiently accurate) measurements of the blood pressure of the subject. Typically that is done by means of regression or parameter estimation, i.e. a modeled functional relation or other mathematical relationship that maps a surrogate physiological characteristic measurement to blood pressure is fitted to the measured surrogate measurements (i.e. the measurements of the physiological characteristics obtained in steps 101 and 103) and the estimated change in blood pressure or the physiological characteristic. As an outcome of the fitting (mapping), the values for the one or more calibration parameters are obtained.

Once the one or more calibration parameters have been determined in step 109, the control unit 4 or the first blood pressure measurement device 8 (as appropriate) can use the one or more calibration parameters to determine blood pressure measurements of the subject. This step is not shown in FIG. 3. In particular, the control unit 4 can control or trigger the first blood pressure measurement device 8 to obtain at least one further physiological characteristic measurement (which is referred to as the 'third' physiological characteristic measurement). The one or more calibration parameters determined in step 109 are used in the mathematical function that relates the third physiological characteristic measurement (e.g. PTT or PWV) to blood pressure. This blood pressure measurement is referred to as a 'calibrated measurement' of blood pressure. The physiological characteristic can be continuously or semi-continuously measured to provide a continuous or semi-continuous measurement of the blood pressure of the subject.

As noted above, in some embodiments the control unit 4 can cause the change in posture of the subject 30. Thus, in some embodiments, the method further comprises a step of causing a change in the posture of the torso 34 between steps 101 and 103. In some cases the control unit 4 can provide an instruction or command to the subject 30 or to a care provider (for example an audio and/or visual instruction) so that the subject 30 changes their posture themselves, or the care provider changes the subject's posture, for example by changing the angle of the bed that the subject 30 is lying on or changing the angle of the chair that the subject 30 is sitting on. Alternatively the control unit 4 can output a control signal to the actuator 12 in order to automatically change the angle of the bed or chair on which the subject 30 is lying or sitting. In some embodiments, the control unit 4 can first issue an instruction or command to the subject or care provider that a change in posture is required, and if the change in posture does not occur within a specified time period, the control unit 4 can output a control signal to the actuator 12 in order to automatically change the angle of the bed or chair on which the subject 30 is lying or sitting.

In embodiments where the control unit 4 caused the change in posture (e.g. by controlling the actuation of the bed or chair angle), after obtaining the second measurement of the physiological characteristic in step 103, the control unit 4 may control the actuator 12 to return the bed or chair to the original angle (e.g. the angle for the first physiological characteristic measurement in step 101).

In some embodiments, to make sure that the second physiological characteristic measurement in step 103 is reliable, the control unit 4 can analyse the physiological characteristic measurement made by the first blood pressure measurement device 8 to determine if the physiological characteristic is stable (i.e. constant) at the time of the second physiological characteristic measurement. That is, after the posture of the torso changes, it may take a few seconds (or longer) for the blood pressure of the subject to adjust, and thus it can be useful to wait for a certain time for the physiological characteristic to stabilise before obtaining the second physiological characteristic measurement in step 103. Thus, in some embodiments, the control unit 4 can analyse the measurement of the physiological characteristic, for example the PWV, the PAT, the PTT, or analyse relevant characteristics of the measurement signal itself (i.e. the characteristics relevant to determining the blood pressure), e.g. the PPG signal, the accelerometer signal or the ECG signal, to determine if the relevant characteristics are constant or substantially constant (i.e. they do not vary by more than a threshold amount) during a time period. If the physiological characteristics are not constant (or not substantially constant), the control unit 4 can wait until they are constant or substantially constant before obtaining the second physiological characteristic measurement in step 103.

The method in FIG. 3 can be performed when the first blood pressure measurement device 8 is first activated. In some embodiments, the method in FIG. 3 can be repeated periodically to determine a new or updated calibration parameter. Alternatively the method in FIG. 3 can be repeated after a certain time has elapsed since the calibration parameter was determined. As another alternative, the method in FIG. 3 can be repeated when features or characteristics in the surrogate physiological characteristic measurement have changed considerably. For example, the method in FIG. 3 can be repeated when the difference of a feature or physiological characteristic measurement compared with its value from the time of the last calibration measurement exceeds a defined threshold. In a specific example, in the case of a PPG signal, a considerable change can be considered as a change in the amplitude (i.e. the AC value) of the PPG signal by 10%. In another specific example, in the case of a PPG signal, a considerable change can be considered as a change in the DC value of the PPG signal by 10%. As another alternative, the method in FIG. 3 can be repeated when the difference between a blood pressure measurement determined from the physiological characteristic measurement compared with a blood pressure measurement determined from a physiological characteristic measurement obtained just after the calibration parameter was determined (e.g. the third physiological characteristic measurement) exceeds a defined threshold. In yet another alternative, measurements from another sensor that measures a physiological characteristic of the subject can be used to determine if a recalibration needs to be performed. The physiological characteristic can be heart rate, the presence of arrhythmia, a change in fluid volume, etc.

It will be appreciated that although the method in FIG. 3 only requires a single measurement by the first blood pressure measurement device 8 before and after the change in blood pressure occurs, it would be possible to perform the calibration using additional physiological characteristic measurements. In this case, the method could comprise obtaining a measurement of the physiological characteristic when the torso is in a third posture (that is different to the first and second postures), estimating a change in blood pressure of the subject 30 based on the change in posture to the third posture and then determining a calibration parameter using the three physiological characteristic measurements and the two estimates of blood pressure change.

Figure 7:
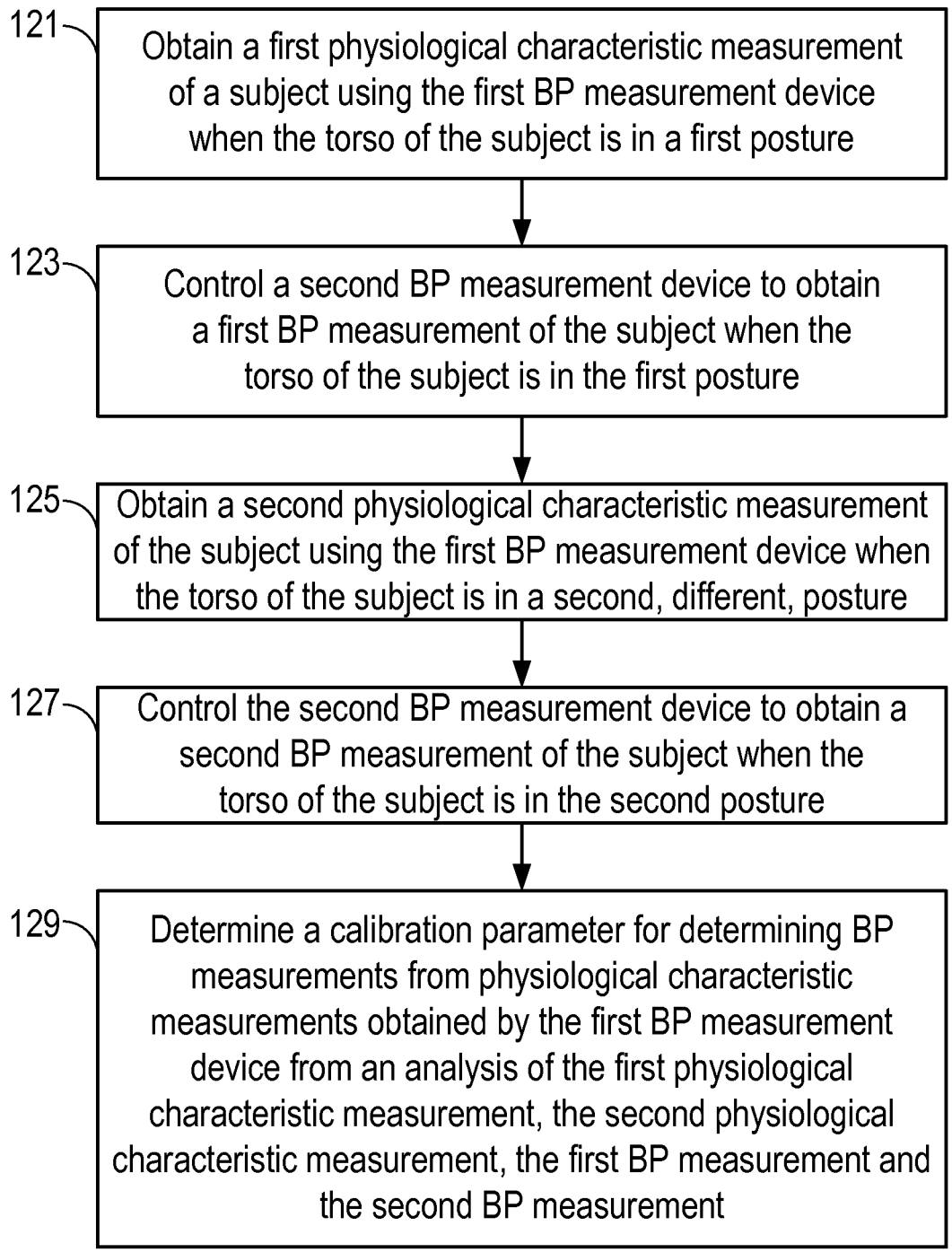
FIG. 7 is a flow chart illustrating a method according to an alternative aspect.

The flow chart in FIG. 7 illustrates a method of determining a calibration parameter for the first blood pressure measurement device 8 in accordance with a second aspect. In this aspect, rather than estimating a change in the blood pressure as a result of the change in posture of the torso in step 107, the method according to the second aspect uses a second blood pressure measurement device 14 to obtain reference blood pressure measurements in the first posture and the second posture and uses these reference measurements to determine the calibration parameters.

These reference blood pressure measurements may be obtained in a relatively short space of time (e.g. a few seconds or up to a minute or two apart). Where the second blood pressure measurement device 14 uses a cuff to obtain the blood pressure measurements, it can be difficult to obtain two reliable blood pressure measurements in this period of time as it can take several minutes for the blood flow to return to a normal state after a cuff is deflated. Thus, in some embodiments, to avoid this problem, the second blood pressure measurement device 14 can comprise means to enable measurements to be obtained from two different sites on the subject's body (e.g. from both arms). Thus, in some embodiments the second blood pressure measurement device 14 comprises two inflatable cuffs and respective sensors (e.g. sound sensors in the case of an auscultatory measurement and pressure sensors in the case of an oscillometric measurement) that are used on different limbs (e.g. different arms), with one cuff being used to obtain one of the blood pressure measurements and the other cuff being used to obtain the other blood pressure measurement. It will be appreciated that in embodiments in which the second blood pressure measurement device 10 comprises means to enable measurements to be obtained from two different sites on the subject's body, the second blood pressure measurement device 10 may comprise two separate blood pressure measurement devices. This has several advantages in that the calibration process is less uncomfortable for the subject (since using the same cuff twice in a short space of time can be painful), the calibration process is more reliable since there is no influence on the second measurement from the first measurement, and the measurements can be performed quicker, since it is not necessary to complete the deflation of one cuff before starting the inflation of the other.

The method in FIG. 7 can be implemented or performed by the control unit 4. Since the first blood pressure measurement device 8 is to be used to continuously or semi-continuously to measure a physiological characteristic in the subject 30 and requires calibration before sufficiently accurate blood pressure measurements can be obtained from those physiological characteristic measurements, the method of FIG. 7 can be performed when the first blood pressure measurement device 8 is first activated. The method of FIG. 7 can also be performed periodically in order to recalibrate the first blood pressure measurement device 8 (e.g. every few minutes or every hour, etc.) or as required (e.g. when the physiological characteristic being measured by the first blood pressure measurement device 8 has changed by more than a threshold amount).

In step 121, a measurement of the surrogate physiological characteristic of the subject is obtained using the first blood pressure measurement device 8. This step may comprise the control unit 4 outputting a suitable control or trigger signal to the first blood pressure measurement device 8 to cause the first blood pressure measurement device 8 to perform a physiological characteristic measurement, or, since the first blood pressure measurement device 8 may be continuously measuring the physiological characteristic, this step may comprise the control unit 4 receiving or obtaining the most recent physiological characteristic measurement from the first blood pressure measurement device 8. This physiological characteristic measurement is referred to as the 'first' physiological characteristic measurement and is obtained when the torso of the subject is in a 'first' posture. As in the first aspect, this posture can be lying down (face up, face down or lying on the side), e.g. with the torso at an angle of 0° with respect to a horizontal plane, sitting upright (e.g. with the torso at an angle of 90° with respect to the horizontal plane), or lying an angle between a flat and upright posture (e.g. with the torso at an angle between 0° and 90° with respect to the horizontal plane).

As in the first aspect, in preferred embodiments the physiological characteristic is measured at a central site on the body in order to derive a central measurement of the blood pressure. For example the physiological characteristic can be the pulse wave velocity (PWV) which is derived from the pulse transit time (PTT), which is itself determined by measuring the arrival of a pulse at two different locations in the body of the subject (e.g. in the femoral artery and carotid artery). Thus step 121 can comprise obtaining a measurement of the arrival time of a pulse at two locations and deriving the PTT and PWV therefrom.

In step 123, the second blood pressure measurement device 14 is controlled by the control unit 4 to obtain a blood pressure measurement of the subject 30 (for example by the control unit 4 outputting a suitable control or trigger signal to the second blood pressure measurement device 14). This blood pressure measurement is referred to as the 'first' blood pressure measurement or a 'first calibration measurement'. Steps 121 and 123 can be performed at the same time, or performed (in either order) sufficiently close in time that no change in the blood pressure of the subject 30 will have occurred between the taking of the first physiological characteristic measurement and the first blood pressure measurement. For example the first physiological characteristic measurement and the first blood pressure measurement can be obtained during the same breathing cycle (i.e. within the same breath). Alternatively, for subjects with a stable blood pressure (i.e. where the blood pressure is relatively constant over time), the time between the first physiological characteristic measurement and the first blood pressure measurement can be a few seconds, or even a few minutes.

Next, in step 125, which takes place when the torso of the subject is in a different (second) posture to that used in step 121, and specifically takes place when the site at which the surrogate measure of blood pressure is being measured is at a different height with respect to the heart than in step 121 (i.e. the torso is at a different angle in step 125 than in steps 121/123), subject 30, the control unit 4 obtains another measurement of the physiological characteristic using the first blood pressure measurement device 8. This physiological characteristic measurement is referred to as the 'second' physiological characteristic measurement. As with step 121, since the first physiological characteristic measurement device 8 is monitoring the physiological characteristic continuously or semi-continuously, step 125 may comprise the control unit 4 obtaining a current physiological characteristic measurement from the first blood pressure measurement device 8, rather than the control unit 4 explicitly requesting a physiological characteristic measurement at that time. Alternatively however, this step can comprise the control unit 4 controlling the first blood pressure measurement device 8 to make a measurement of the physiological characteristic.

It will be appreciated that for the calibration parameter to be determined, the difference in the postures (angle) between steps 121/123 and 125 should be sufficient for there to be a change in the blood pressure of the subject. Thus, it is not necessarily required for the torso of the subject to change between a flat lying posture and an upright posture (or vice versa). Typically an angular change of the torso of 10° to 20° from a flat lying positing towards an upright posture is sufficient to generate a blood pressure difference larger than the typical error spread of 4 to 8 mmHg for oscillometric BP measurement devices, and thus the posture change between steps 121/123 and 125 can be of the order of 10° or more.

While the torso of the subject 30 is in the second posture, the control unit 4 also controls the second blood pressure measurement device 14 to obtain another blood pressure measurement of the subject 30 (step 127). This blood pressure measurement is referred to the 'second' blood pressure measurement or a 'second' calibration measurement'. As noted above, in some embodiments the second blood pressure measurement device 14 can include means to enable the second blood pressure measurement device 14 to obtain blood pressure measurements from two different sites on the subject's body. For example the second blood pressure measurement device 14 can comprise two inflatable cuffs, in which case step 127 can comprise obtaining the second blood pressure measurement 14 using a different cuff to that used in step 123 to obtain the second blood pressure measurement.

As with the first physiological characteristic measurement and the first blood pressure measurement, steps 125 and 127 can be performed at the same time, or they can be performed sufficiently close in time (in either order) that no change in the blood pressure of the subject 30 will have occurred between the taking of the second physiological characteristic measurement and the second blood pressure measurement. The other requirements described above for the relative timing of the first physiological characteristic measurement and the first blood pressure measurement can apply also to the relative timing of the second physiological characteristic measurement and the second blood pressure measurement.

After step 127, the control unit 4 determines one or more calibration parameters for the first blood pressure measurement device 8 from an analysis of the first physiological characteristic measurement, the second physiological characteristic measurement, the first blood pressure measurement and the second blood pressure measurement (step 129). That is, the control unit 4 determines one or more calibration parameters that are to be applied to subsequent physiological characteristic measurements by the first blood pressure measurement device 8 in order to provide accurate (or sufficiently accurate) measurements of the blood pressure of the subject 30. Typically that is done by means of regression, i.e. a modeled functional relation or other mathematical relationship that maps a surrogate physiological characteristic measurement to blood pressure is fitted to the measured surrogate measurements (i.e. the measurements of the physiological characteristics obtained in steps 121 and 125) and blood pressure measurements from the second blood pressure measurement device 14. As an outcome of the fitting (mapping), the values for the one or more calibration parameters are obtained.

Once the one or more calibration parameters have been determined in step 129, the control unit 4 or the first blood pressure measurement device 8 (as appropriate) can use the one or more calibration parameters to determine blood pressure measurements of the subject 30. This step is not shown in FIG. 7. In particular, the control unit 4 can control or trigger the first blood pressure measurement device 8 to obtain at least one further physiological characteristic measurement (which is referred to as the 'third' physiological characteristic measurement). The one or more calibration parameters determined in step 129 are used in the mathematical function that relates the third physiological characteristic measurement (e.g. PAT) to blood pressure. This blood pressure measurement is referred to as a 'calibrated measurement' of blood pressure. The physiological characteristic can be continuously or semi-continuously measured to provide a continuous or semi-continuous measurement of the blood pressure of the subject.

After the one or more calibration parameters have been determined in step 129 (or perhaps once the second physiological characteristic measurement and second blood pressure measurement have been obtained in steps 125 and 127), the second blood pressure measurement device 14 can be deactivated (i.e. the cuff deflated, if the second blood pressure measurement device 14 comprises a cuff), since it is only required for determining the one or more calibration parameters. The second blood pressure measurement device 14 may subsequently be reactivated or used when a calibration parameter is to be updated.

In some embodiments the control unit 4 can cause the change in posture of the subject 30. Thus, in some embodiments, the method further comprises a step of causing a change in the posture of the torso 34 between steps 123 and 125. In some cases the control unit 4 can provide an instruction or command to the subject 30 or to a care provider (for example an audio and/or visual instruction) so that the subject 30 changes their posture themselves, or the care provider changes the subject's posture, for example by changing the angle of the bed that the subject 30 is lying on or changing the angle of the chair that the subject 30 is sitting on. Alternatively the control unit 4 can output a control signal to the actuator 12 in order to automatically change the angle of the bed or chair on which the subject 30 is lying or sitting. In some embodiments, the control unit 4 can first issue an instruction or command to the subject or care provider that a change in posture is required, and if the change in posture does not occur within a specified time period, the control unit 4 can output a control signal to the actuator 12 in order to automatically change the angle of the bed or chair on which the subject 30 is lying or sitting.

In embodiments where the control unit 4 caused the change in posture (e.g. by controlling the actuation of the bed or chair angle), after obtaining the second measurement of the physiological characteristic in step 125 and the second blood pressure measurement in step 127, the control unit 4 may control the actuator 12 to return the bed or chair to the original angle (e.g. the angle for the first physiological characteristic measurement in step 121).

In some embodiments, to make sure that the first blood pressure measurement and the second blood pressure measurement are reliable, the control unit 4 can analyse the physiological characteristic measurement made by the first blood pressure measurement device 8 to determine if the blood pressure is stable (i.e. constant) at the time of the blood pressure measurement by the second blood pressure measurement device 14. In particular, the control unit 4 can analyse the measurement of the physiological characteristic, for example the PWV, the PAT, the PTT, or analyse relevant characteristics of the measurement signal itself (i.e. the characteristics relevant to determining the blood pressure), e.g. the PPG signal, the accelerometer signal or the ECG signal, to determine if the relevant characteristics are constant or substantially constant (i.e. they do not vary by more than a threshold amount) during the period in which the second blood pressure measurement device 10 is measuring the blood pressure. If the physiological characteristics are not constant (or not substantially constant), the control unit 4 can discard that blood pressure measurement by the second blood pressure measurement device 14 and perform a new measurement when the physiological characteristics are determined to be constant or substantially constant. In this case, a new physiological characteristic measurement by the first blood pressure measurement device 8 may also be required since measurements are required by both devices 8, 14 simultaneously (or generally at the same time).

The method in FIG. 7 can be performed when the first blood pressure measurement device 8 is first activated. In some embodiments, the method in FIG. 7 can be repeated periodically to determine a new or updated calibration parameter. Alternatively the method in FIG. 7 can be repeated after a certain time has elapsed since the calibration parameter was determined. As another alternative, the method in FIG. 7 can be repeated when features or characteristics in the surrogate measurement (i.e. the measurement of the physiological characteristic that is used to determine the blood pressure) have changed considerably. For example, the method in FIG. 7 can be repeated when the difference of a feature or physiological characteristic measurement compared with its value from the time of the last calibration measurement exceeds a defined threshold. In a specific example, in the case of a PPG signal, a considerable change can be considered as a change in the amplitude (i.e. the AC value) of the PPG signal by 10%. In another specific example, in the case of a PPG signal, a considerable change can be considered as a change in the DC value of the PPG signal by 10%. As another alternative, the method in FIG. 7 can be repeated when the difference between a blood pressure measurement determined from the physiological characteristic measurement compared with a blood pressure measurement determined from a physiological characteristic measurement obtained just after the calibration parameter was determined (e.g. the third physiological characteristic measurement) exceeds a defined threshold. In yet another alternative, measurements from another sensor that measures a physiological characteristic of the subject can be used to determine if a recalibration needs to be performed. The physiological characteristic can be heart rate, the presence of arrhythmia, a change in fluid volume, etc.

It will be appreciated that although the method in FIG. 7 only requires a single measurement by each blood pressure measurement device 8, 14 before and after the change in blood pressure occurs, it would be possible to perform the calibration using further pairs of physiological characteristic measurements and blood pressure measurements. In this case, the method could comprise obtaining measurements of the physiological characteristic and blood pressure when the torso is in a third posture (that is different to the first and second postures), and then steps 125 and 127 can be performed at that different blood pressure.

There is therefore provided an improved method and apparatus for calibrating measurements of blood pressure obtained by a blood pressure measurement device.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other processing unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining a calibration parameter for a first blood pressure, BP, measurement device, the method comprising:
   obtaining a first physiological characteristic measurement of a subject using the first BP measurement device, wherein the first BP measurement device is for obtaining physiological characteristic measurements of a physiological characteristic of the subject and for determining a BP measurement of the subject from the physiological characteristic measurements using the calibration parameter, wherein the first physiological characteristic measurement is obtained when a torso of the subject is in a first posture;

obtaining a second physiological characteristic measurement of the subject using the first BP measurement device, wherein the second physiological characteristic measurement is obtained when the torso of the subject is in a second, different, posture;

determining a change in posture of the torso of the subject from the first posture of the subject to the second posture of the subject;

estimating, without measuring, a change in a BP of the subject or a change in the physiological characteristic of the subject from the determined change in the posture of the torso; and determining the calibration parameter for determining a future BP measurement from a future physiological characteristic measurement obtained by the first BP measurement device, based on analysis of the first physiological characteristic measurement obtained in the first posture, the second physiological characteristic measurement obtained in the second posture, and the estimated change.

2. The method as claimed in claim 1, the method further comprising, after the step of obtaining the first physiological characteristic measurement, the step of:

causing the change in the posture of the torso of the subject from the first posture to the second posture.

3. The method as claimed in claim 2, wherein the step of causing the change in the posture comprises:

providing an instruction or command to the subject or a care provider for the subject that the posture of the torso of the subject is to be changed; or outputting a control signal to an actuator for a bed or chair associated with the subject to change an angle of the bed or chair.

4. The method as claimed in claim 1, wherein the step of determining the change in the posture of the torso from the first posture to the second posture comprises analyzing analysing a measurement signal from a posture sensor.

5. The method as claimed in claim 1, wherein the first BP measurement device comprises a physiological characteristic sensor for measuring the physiological characteristic of the subject, and wherein the step of determining the change in the posture of the torso from the first posture to the second posture comprises analyzing measurement signal from the physiological characteristic sensor.

6. The method as claimed in claim 1, wherein the step of estimating the change in the BP of the subject from the determined change in the posture of the torso comprises:

estimating a change in height of a location on the body at which the physiological characteristic is measured relative to a heart of the subject from the first posture to the second posture based on the determined change in posture.

7. The method as claimed in claim 1, wherein the physiological characteristic is pulse transit time, PTT, that is obtained by measurements of pulse arrival at two different locations on the body of the subject that are separated by a length l, and wherein the step of estimating the change in the physiological characteristic of the subject from the determined change in the posture of the torso comprises:

evaluating $$PTT(\alpha) = -\frac{1}{m\varrho g\sin(\alpha)}\ln\left|1 - \frac{m\varrho g l\sin(\alpha)}{mP+n}\right|$$

for each of the first and second postures, where p is the density of blood, g is acceleration due to gravity, P is the blood pressure, a is the angle of the torso with respect to the horizontal and m and n are calibration parameters.

8. The method as claimed in claim 1, wherein, after obtaining the first physiological characteristic measurement, the method comprises:

analyzing a signal from the first BP measurement device to determine whether the physiological characteristic is stable; and obtaining the second physiological characteristic measurement if the physiological characteristic is determined to be stable.

9. A computer program product comprising a non-transitory computer-readable storage medium having computer-readable code embodied therein, the computer-readable code being configured such that, on execution by a computer or processor, the computer or processor is caused to perform the method of claim 1.

10. An apparatus for determining a calibration parameter for a first blood pressure, BP, measurement device, the apparatus comprising:

a control unit that is to be coupled to a first BP measurement device that is for obtaining physiological characteristic measurements of a physiological characteristic of a subject and for determining a blood pressure measurement of the subject from the physiological characteristic measurements, wherein the control unit is configured to:

obtain a first physiological characteristic measurement of the subject using the first BP measurement device, wherein the first physiological characteristic measurement is obtained when a torso of the subject is in a first posture;

obtain a second physiological characteristic measurement of the subject using the first BP measurement device, wherein the second physiological characteristic measurement is obtained when the torso of the subject is in a second, different, posture;

determine a change in posture of the torso of the subject from the first posture of the subject to the second posture of the subject;

estimate, without measuring, a change in a BP of the subject or a change of the physiological characteristic of the subject from the determined change in the posture of the torso of the subject; and determine the calibration parameter for determining a future BP measurement from a future physiological characteristic measurement obtained by the first BP measurement device, based on analysis of the first physiological characteristic measurement obtained in the first posture, the second physiological characteristic measurement obtained in the second posture, and the estimated change.

11. The apparatus as claimed in claim 10, wherein the control unit is further configured to cause the change in the posture of the torso of the subject from the first posture to the second posture after obtaining the first physiological characteristic measurement.

12. The apparatus as claimed in claim 11, wherein the control unit is configured to cause the change in the posture by providing an instruction or command to the subject or a care provider for the subject that the posture of the torso of the subject is to be changed; or outputting a control signal to an actuator for a bed or chair associated with the subject to change an angle of the bed or chair.

13. The apparatus as claimed in claim 10, wherein the control unit is configured to determine the change in the posture of the torso from the first posture to the second posture by analyzing a measurement signal from a posture sensor.

14. The apparatus as claimed in claim 10, wherein the first BP measurement device comprises a physiological characteristic sensor for measuring the physiological characteristic of the subject, and wherein the control unit is configured to determine the change in the posture of the torso from the first posture to the second posture by analyzing a measurement signal from the physiological characteristic sensor.

15. The apparatus as claimed in claim 10, wherein the control unit is further configured to analyze a signal from the first BP measurement device to determine whether the physiological characteristic is stable after obtaining the first physiological characteristic measurement; and to obtain the second physiological characteristic measurement if the physiological characteristic is determined to be stable.

\* \* \* \* \*